US005783567A

United States Patent [19]
Hedley et al.

[11] Patent Number: 5,783,567
[45] Date of Patent: Jul. 21, 1998

[54] MICROPARTICLES FOR DELIVERY OF NUCLEIC ACID

[75] Inventors: Mary Lynne Hedley, Belmont, Mass.; Joanne M. Curley, San Mateo, Calif.; Robert S. Langer, Newton, Mass.

[73] Assignee: Pangaea Pharmaceuticals, Inc., Cambridge, Mass.

[21] Appl. No.: 787,547

[22] Filed: Jan. 22, 1997

[51] Int. Cl.$^6$ .................. A61K 48/00; C12N 15/63; C12N 15/11
[52] U.S. Cl. ................ 514/44; 435/320.1; 536/23.1
[58] Field of Search ................ 514/44; 435/320.1; 536/23.1

[56] References Cited

U.S. PATENT DOCUMENTS

| | | | |
|---|---|---|---|
| 4,293,539 | 10/1981 | Ludwig et al. | 424/489 |
| 4,741,872 | 5/1988 | De Luca et al. | 264/4.7 |
| 4,818,542 | 4/1989 | De Luca et al. | 424/491 |
| 5,075,109 | 12/1991 | Tice et al. | 424/193.1 |
| 5,160,745 | 11/1992 | De Luca et al. | 424/487 |
| 5,407,609 | 4/1995 | Tice et al. | 264/4.6 |
| 5,531,925 | 7/1996 | Landh et al. | 252/299.01 |
| 5,580,859 | 12/1996 | Felgner et al. | 514/44 |

FOREIGN PATENT DOCUMENTS

| | | |
|---|---|---|
| 2126685 | 5/1994 | Canada . |
| 248 531 | 12/1987 | European Pat. Off. . |
| 266 119 | 5/1988 | European Pat. Off. . |
| 467 389 | 1/1992 | European Pat. Off. . |
| 635 261 | 1/1995 | European Pat. Off. . |
| 706 792 | 4/1996 | European Pat. Off. . |
| WO 94/04171 | 3/1994 | WIPO . |
| WO 94/09898 | 5/1994 | WIPO . |
| WO 94/23699 | 10/1994 | WIPO . |
| WO 94/23738 | 10/1994 | WIPO . |
| WO 94/28873 | 12/1994 | WIPO . |
| WO 94/28874 | 12/1994 | WIPO . |
| WO 95/07072 | 3/1995 | WIPO . |
| WO 95/17167 | 6/1995 | WIPO . |
| WO 95/20660 | 8/1995 | WIPO . |
| WO 95/24929 | 9/1995 | WIPO . |
| WO 95/35097 | 12/1995 | WIPO . |
| WO 96/00295 | 1/1996 | WIPO . |
| WO 96/11671 | 4/1996 | WIPO . |
| WO 96/29998 | 10/1996 | WIPO . |

OTHER PUBLICATIONS

Amagai et al., "Autoantibodies against a Novel Epithelial Cadherin in Pemphigus Vulgaris, a Disease of Cell Adhesion," *Cell*, 67:869–877, 1991.

Gref et al., "Biodegradable Long–Circulating Polymeric Nanospheres," *Science*, 263:1600–1603, 1994.

Heard, "HLA and autoimmune disease," *HLA & Disease*, pp. 123–151, 1994.

Hedley, "Genetic Modulation of Antigen Presentation," *MHC Molecules: Expression, Assembly & Function*, Ch. 17, pp. 281–294; Editors, Robert G. Urban and Roman M. Chicz; published by R.G. Landes & Co., 1996.

Jones et al., "Immune Responses Following Oral and Parenteral Administration of Plasmid DNA Encapsulated in Poly(lactide–coglycolide) Microparticles," Int'l Meeting on Nucleic Acid Vaccines, Bethesda, MD, 1996.

Lewis et al., "Biodegradable poly(L–lactic acid) matrices for the sustained delivery of antisense oligo–nucleotides," *J. Controlled Release*, 37:173–183, 1995.

Murphy et al., "A novel MHC class II epitope expressed in thymic medulla but not cortex," *Nature*, 338:765–768, 1989.

Shimoda et al., "HLA DRB4 0101–restricted Immunodominant T Cell Autoepitope of Pyruvate Dehydrogenase Complex in Primary Biliary Cirrhosis . . . . " *J. Exp. Med.*, 181:1835–1845, 1995.

Steinman, "Escape from 'Horror Autoxicus': Pathogenesis and Treatment of Autoimmune Disease," *Cell*, 80:7–10, 1995.

Tomlinson et al., "Controllable gene therapy Pharmaceutics of non–viral gene delivery systems," *J. Controlled Release*, 39:357–372, 1996.

*Primary Examiner*—Nancy Degen
*Assistant Examiner*—John S. Brusca
*Attorney, Agent, or Firm*—Fish & Richardson P.C.

[57] ABSTRACT

Disclosed is a preparation of microparticles made up of a polymeric matrix and a nucleic acid expression vector. The polymeric matrix includes one or more synthetic polymers having a solubility in water of less than about 1 mg/l. At least 90% of the microparticles have a diameter less than about 100 microns. The nucleic acid is either RNA, at least 50% of which is in the form of closed circles, or circular DNA plasmid molecules, at least 50% of which are supercoiled.

32 Claims, 9 Drawing Sheets

5,783,567

1

MICROPARTICLES FOR DELIVERY OF NUCLEIC ACID

BACKGROUND OF THE INVENTION

This invention relates to methods of delivering nucleic acids into cells.

Gene therapy is a highly promising technique for treatment of hereditary diseases, e.g., cystic fibrosis. Gene therapy can also be used when expression of gene products from genes which are not naturally found in the host cells is desired, for example, from genes encoding cytotoxic proteins targeted for expression in cancer cells.

Gene therapy can fall into several categories. It is sometimes desirable to replace a defective gene for the entire lifespan of a mammal, as in the case of an inherited disease such as cystic fibrosis, phenylketonuria, or severe combined immunodeficiency disease (SCID). In other cases, one may wish to treat a mammal with a gene that will express a therapeutic polypeptide for a limited amount of time, e.g., during an infection. Nucleic acids in the form of antisense oligonucleotides or ribozymes are also used therapeutically. Moreover, polypeptides encoded by nucleic acids can be effective stimulators of the immune response in mammals.

Various techniques have been used for introducing genes into cells, including infection with viral vectors, biolistic transfer, injection of "naked" DNA (U.S. Pat. No. 5,580, 859), and delivery via liposomes or polymeric particles.

SUMMARY OF THE INVENTION

The invention is based on the discovery that microparticles containing nucleic acids having an appropriate size for phagocytosis can be made without adversely affecting nucleic acid integrity. These microparticles are highly effective vehicles for the delivery of polynucleotides into phagocytic cells.

In general, the invention features a preparation of microparticles, each of which includes a polymeric matrix and a nucleic acid expression vector. The polymeric matrix includes one or more synthetic polymers having a solubility in water of less than about 1 mg/l; in the present context, synthetic is defined as non-naturally occurring. At least 90% of the microparticles have a diameter less than about 100 microns. The nucleic acid is either RNA, at least 50% (and preferably at least 70% or even 80%) of which is in the form of closed circles, or circular DNA plasmid molecules, at least 50% (and preferably at least 70% or even 80%) of which are supercoiled. In some cases, it is desirable for at least 90% of the microparticles to have a diameter less than about 20 microns, and preferably less than about 11 microns.

Another embodiment of the invention features a microparticle less than about 20 microns in diameter, including a polymeric matrix and nucleic acid. The polymeric matrix is made from one or more synthetic polymers having a solubility in water of less than about 1 mg/l. At least 50% (and preferably at least 70% or even 80%) of the nucleic acid molecules are in the form of supercoiled DNA.

The polymeric matrix can be biodegradable. Biodegradable is used here to mean that the polymers degrade over time into compounds which are known to be cleared from the host cells by normal metabolic pathways. Generally, a biodegradable polymer will be substantially metabolized within about 1 month after injection into a patient, and certainly within about 2 years. In certain cases, the polymeric matrix can be made of a single synthetic, biodegradable copolymer, e.g., poly-lactic-co-glycolic acid (PLGA).

2

The ratio of lactic acid to glycolic acid in the copolymer can be within the range of about 1:2 to about 4:1 by weight, preferably within the range of about 1:1 to about 2:1 by weight, and most preferably about 65:35 by weight. In some cases, the polymeric matrix also includes a targeting molecule such as a ligand, receptor, or antibody, to increase the specificity of the microparticle for a given cell type or tissue type.

For certain applications, the microparticle has a diameter of less than about 11 microns. The microparticle can be suspended in an aqueous solution (e.g., for delivery by injection) or can be in the form of a dry solid (e.g., for storage or for delivery via inhalation or implantation). The nucleic acid can be an expression control sequence operatively linked to a coding sequence. Expression control sequences include, for example, any nucleic acid sequences known to regulate transcription or translation, such as promoters, enhancers, or silencers. In preferred examples, at least 60% or 70% of the DNA is supercoiled. More preferably, at least 80% is supercoiled.

In another embodiment, the invention features a microparticle less than about 20 microns in diameter, including a polymeric matrix and a nucleic acid molecule (preferably in closed, circular form), wherein the nucleic acid molecule includes an expression control sequence operatively linked to a coding sequence. The expression product encoded by the coding sequence can be a polypeptide at least 7 amino acids in length, having a sequence essentially identical to the sequence of either a fragment of a naturally-occurring mammalian protein or a fragment of a naturally-occurring protein from an agent which infects or otherwise harms a mammal; or a peptide having a length and sequence which permit it to bind to an MHC class I or II molecule. Examples are set forth in WO 94/04171, herein incorporated by reference.

Essentially identical in the context of a DNA or polypeptide sequence is defined here to mean differing no more than 25% from the naturally occurring sequence, when the closest possible alignment is made with the reference sequence and where the differences do not adversely affect the desired function of the DNA or polypeptide in the methods of the invention. The phrase fragment of a protein is used to denote anything less than the whole protein.

The polypeptide and the peptide can each be linked to a trafficking sequence. The term "trafficking sequence" refers to an amino acid sequence which causes a polypeptide to which it is fused to be transported to a specific compartment of the cell, e.g., the nucleus, endoplasmic reticulum, a lysosome, or an endosome.

In the embodiment where the expression product includes a peptide having a length and sequence which permit it to bind an MHC class I or II molecule, the expression product is typically immunogenic. The expression product can have an amino acid sequence that differs from the sequence of a naturally occurring protein recognized by a T cell in the identity of not more than 25% of its amino acid residues, provided that it can still be recognized by the same T cell and can alter the cytokine secretion profile of the T cell (i.e., an "altered peptide ligand").

Examples of expression products include amino acid sequences at least 50% identical to the sequence of a fragment of myelin basic protein (MBP), proteolipid protein (PLP), invariant chain, GAD65, islet cell antigen, desmoglein, α-crystallin, or β-crystallin, where the fragment can bind the MHC class II molecule. Table 1 lists many of such expression products that are thought to be involved in autoimmune disease. Fragments of these proteins can be essentially identical to any one of SEQ ID NOs: 1–46, such as MBP residues 80–102 (SEQ ID NO: 1), PLP residues 170–191 (SEQ ID NO: 2), or invariant chain residues 80–124 (SEQ ID NO: 3). Other fragments are listed in Table 2.

Alternatively, the expression product can include an amino acid sequence essentially identical to the sequence of an antigenic portion of any of the tumor antigens listed in Table 3, such as those encoded by the human papillomavirus E6 and E7 genes, Her2/neu gene, the prostate specific antigen gene, the melanoma antigen recognized by T cells (MART) gene, or the melanoma antigen gene (MAGE).

In still other cases, the expression product includes an amino acid sequence essentially identical to the sequence of an antigenic fragment of a protein naturally expressed by a virus, e.g., a virus which chronically infects cells, such as human papillomavirus (HPV), human immunodeficiency virus (HIV), herpes simplex virus (HSV), hepatitis B virus (HBV), or hepatitis C virus (HCV); a bacterium, such as mycobacteria; or a parasitic eukaryote, such as Plasmodium species. A representative list of class I-binding peptides, including both virus-derived peptides and fragments of tumor antigens, is included in Table 4.

In another embodiment, the invention features a microparticle less than about 20 microns in diameter, including a polymeric matrix and a nucleic acid molecule, wherein the nucleic acid molecule includes an expression control sequence operatively linked to a coding sequence. The expression product encoded by the coding sequence is a

TABLE 1

| Autoantigens | | |
|---|---|---|
| Disease | Associated Antigen | Notes |
| Coeliac disease | α-Gliadin | a |
| Goodpasture's syndrome | Basement membrane collagen | a |
| Graves' disease | Thyroid Stimulating Hormone (TSH) receptor | a |
| Hashimoto's disease | Thyroglobulin | a |
| Isaac's syndrome | voltage-gated potassium channels | b |
| Insulin-dependent diabetes | Glutamic acid decarboxylase (GAD) | a |
| | Insulin receptor | a |
| | Insulin associated antigen (IA-w) | a |
| | Hsp | b |
| Lambert-Eaton myasthenic syndrome (LEMS) | Synaptogamin in voltage-gated calcium channels | b |
| Multiple sclerosis | Myelin basic protein (MBP) | a |
| | Proteolipid protein (PLP) | a |
| | Myelin oligodendrocyte-associated protein (MOG) | a |
| | αB-crystallin | a |
| Myasthenia Gravis | Acetyl choline receptor | a |
| Paraneoplastic encephalitis | RNA-binding protein HuD | b |
| Pemphigus vulgaris | "PeV antigen complex" Desmoglein (DG) | a c |
| Primary Biliary cirrhosis | Dihydrolipoamide acetyltransferase Pyruvate dehydrogenase complex 2 (PDC-E2) | b d |
| Progressive systemic sclerosis | DNA topoisomerase RNA polymerase | a a |
| Rheumatoid arthritis | Immunoglobulin Fc Collagen | a |
| Scleroderma | Topoisomerase I | b |
| Stiff-man syndrome | Glutamic acid decarboxylase (GAD) | a |
| Systemic lupus erythematosus | ds-DNA | a |

TABLE 1-continued

| Autoantigens | | |
|---|---|---|
| Disease | Associated Antigen | Notes |
| Uveitis | Interphotoreceptor retinoid-binding protein | b |
| | S antigen (rod out segment) | b |

References:
a) HLA and Autoimmune Disease, R. Heard, pg. 123–151 in HLA & Disease, Academic Press, New York, 1994, (R. Lechler, ed.)
b) Cell 80, 7-10 (1995)
c) Cell 67, 869-877 (1991)
d) JEM 181, 1835-1845 (1995)

TABLE 2

| Class II Associated Peptides | | |
|---|---|---|
| Peptide | SEQ ID NO: | Source Protein |
| GRTQDENPVVHFFKNIVTPRTPP | 1 | MBP 80-102 |
| AVYVYIYFNTWTTCQFIAFPFK | 2 | PLP 170-191 |
| FKMRMATPLLMQA | 3 | Invariant chain 88-100 |
| TVGLQLIQLINVDEVNQIV TTNVRLKQQWVDYNLKW | 4 | AChR α 32-67 |
| QIVTTNVRLKQQWVDYNLKW | 5 | AChR α 48-67 |
| QWVDYNL | 6 | AChR α 59-65 |
| GGVKKIHIPSEKIWRPDL | 7 | AChR α 73-90 |
| AIVKFTKVLLQY | 8 | AChR α 101-112 |
| WTPPAIFKSYCEIIVTHFPF | 9 | AChR α 118-137 |
| MKLGTWTYDGSVV | 10 | AChR α 144-156 |
| MKLGIWTYDGSVV | 11 | AChR α 144-157 analog(I-148) |
| WTYDGSVVA | 12 | AChR α 149-157 |
| SCCPDTPYLDITYHFVM | 13 | AChR α 191-207 |
| DTPYLDITYHFVMQRLPL | 14 | AChR α 195-212 |
| FIVNVIIPCLLFSFLTGLVFY | 15 | AChR α 214-234 |
| LLVIVELIPSTSS | 16 | AChR α 257-269 |
| STHVMPNWVRKVFIDTIPN | 17 | AChR α 304-322 |
| NWVRKVFIDTIPNIMFFS | 18 | AChR α 310-327 |
| IPNIMFFSTMKRPSREKQ | 19 | AChR α 320-337 |
| AAAEWKYVAMVMDHIL | 20 | AChR α 395-410 |
| IIGTLAVFAGRLIELNQQG | 21 | AChR α 419-437 |
| GQTIEWIFIDPEAFTENGEW | 22 | AChR γ 165-184 |
| MAHYNRVPALPFPGDPRPYL | 23 | AChR γ 476-495 |
| LNSKIAFKIVSQEPA | 24 | desmoglein 3 190-204 |
| TPMFLLSRNTGEVRT | 25 | desmoglein 3 206-220 |
| PLGFFPDHQLDPAFGA | 26 | HBS preS1 10-25 |
| LGFFPDHQLDPAFGANS | 27 | HBS preS1 11-27 |
| FFLLTRILTI | 28 | HBS Ag 19-28 |
| RILTIPQSLD | 29 | HBS Ag 24-33 |
| TPTLVEVSRNLGK | 30 | HSA 444-456 |
| AKTIAYDEEARR | 31 | hsp 65 2-13 |
| VVTVRAERPG | 32 | hsp 18 61-70 |
| SQRHGSKYLATASTMDHARHG | 33 | MBP 7-27 |
| RDTGILDSIGRFFGGDRGAP | 34 | MBP 33-52 |
| QKSHGRTQDENPVVHFFKNI | 35 | MBP 74-93 |
| DENPVVHFFKNIVT | 36 | MBP 84-97 |
| ENPVVHFFKNIVTPR | 37 | MBP 85-99 |
| HFFKNIVTPRTPP | 38 | MBP 90-102 |
| KGFKGVDAQGTLSK | 39 | MBP 139-152 |
| VDAQGTLSKIFKLGGRDSRS | 40 | MBP 144-163 |
| LMQYIDANSKFIGITELKK | 41 | Tetanus Toxoid 828-846 |
| QYIKANSKFIGIT | 42 | Tetanus Toxoid 830-842 |
| FNNFTVSFWLRVPK | 43 | Tetanus Toxoid 947-960 |
| SFWLRVPKVSASHLE | 44 | Tetanus Toxoid 953-967 |
| KFIIKRYTPNNEIDSF | 45 | Tetanus Toxoid 1174-1189 |

TABLE 2-continued

Class II Associated Peptides

| Peptide | SEQ ID NO: | Source Protein |
|---|---|---|
| GQIGNDPNRDIL | 46 | Tetanus Toxoid 1273-1284 |

TABLE 3

Tumor Antigens

| Cancer | Associated Antigen |
|---|---|
| Melanoma | BAGE 2-10 |
| Breast/Ovarian | c-ERB2 (Her2/neu) |
| Burkitt's lymphoma/Hodgkin's lymphoma | EBNA-1 |
| Burkitt's lymphoma/Hodgkin's lymphoma | EBNA-2 |
| Burkitt's lymphoma/Hodgkin's lymphoma | EBNA-3 |
| Burkitt's lymphoma/Hodgkin's lymphoma | EBNA-3A |
| Burkitt's lymphoma/Hodgkin's lymphoma | EBNA-3C |
| Burkitt's lymphoma/Hodgkin's lymphoma | EBNA-4 |
| Burkitt's lymphoma/Hodgkin's lymphoma | EBNA-6 |
| Burkitt's lymphoma/Hodgkin's lymphoma | EBV |
| Burkitt's lymphoma/Hodgkin's lymphoma | EBV LMP2A |
| Melanoma | GAGE-1 |
| Melanoma | gp75 |
| Cervical | HPV 16 E6 |
| Cervical | HPV 16 E7 |
| Cervical | HPV 18 E6 |
| Cervical | HPV 18 E7 |
| Melanoma | MAG |
| Melanoma | MAGE-1 |
| Melanoma | MAGE-2 |
| Melanoma | MAGE-3 |
| Melanoma | MAGE-4b |
| Melanoma | MAGE-5 |
| Melanoma | MAGE-6 |
| Melanoma | MART-1/Melan-A |
| Pancreatic/Breast/Ovarian | MUC-1 |
| Melanoma | MUM-1-B |
| Breast/Colorectal/Burkitt's lymphoma | p53 |
| Melanoma | Pmel 17 (gp100) |
| Prostate | PSA Prostate Specific Antigen |
| Melanoma | Tyrosinase |
| | CEA Carcinoembryonic Antigen |
| | LRP Lung Resistance Protein |
| | Bcl-2 |
| | Ki-67 |

TABLE 4

Class I associated tumor and pathogen peptides

| Peptide | SEQ ID NO: | Source Protein |
|---|---|---|
| AARAVFLAL | 47 | BAGE 2-10 |
| YRPRPRRY | 48 | GAGE-1 9-16 |
| EADPTGHSY | 49 | MAGE-1 161-169 |
| SAYGEPRKL | 50 | MAGE-1 230-238 |
| EVDPIGHLY | 51 | MAGE-3 161-169 |
| FLWGPRALV | 52 | MAGE-3 271-279 |
| GIGILTV | 53 | MART-1 29-35 |
| ILTVILGV | 54 | MART-1 32-39 |
| STAPPAHGV | 55 | MUC-1 9-17 |
| EEKLIVVLF | 56 | MUM-1 261-269 |
| MLLAVLYCL | 57 | TYROSINASE 1-9 |
| SEIWRDIDF | 58 | TYROSINASE 192-200 |
| AFLPWHRLF | 59 | TYROSINASE 206-214 |
| YMNGTMSQV | 60 | TYROSINASE 369-376 |
| KTWGQYWQV | 61 | PMEL 17 (GP100) 154-162 |
| ITDQVPFSV | 62 | PMEL 17 (GP100) 209-217 |
| YLEPGPTVA | 63 | PMEL 17 (GP100) 280-288 |
| LLDGTATLRL | 64 | PMEL 17 (GP100) 476-485 |

TABLE 4-continued

Class I associated tumor and pathogen peptides

| Peptide | SEQ ID NO: | Source Protein |
|---|---|---|
| ELNEALELEK | 65 | p53 343-351 |
| STPPPGTRV | 66 | p53 149-157 |
| LLPENNVLSPL | 67 | p53 25-35 |
| LLGRNSFEV | 68 | p53 264-272 |
| RMPEAAPPV | 69 | p53 65-73 |
| KIFGSLAFL | 70 | HER-2/neu 369-377 |
| IISAVVGIL | 71 | HER-2/neu 654-662 |
| CLTSTVQLV | 72 | HER-2/neu 789-797 |
| YLEDVRLV | 73 | HER-2/neu 835-842 |
| VLVKSPNHV | 74 | HER-2/neu 851-859 |
| RFRELVSEFSRM | 75 | HER-2/neu 968-979 |
| LLRLSEPAEL | 76 | PSA 119-128 |
| DLPTQEPAL | 77 | PSA 136-144 |
| KLQCVDLHV | 78 | PSA 166-174 |
| VLVASRGRAV | 79 | PSA 36-45 |
| VLVHPQWVL | 80 | PSA 49-57 |
| DMSLLKNRFL | 81 | PSA 98-107 |
| QWNSTAFHQ | 82 | HBV envelope 121-130 |
| VLQAGFF | 83 | HBV envelope 177-184 |
| LLLCLIFL | 84 | HBV envelope 250-257 |
| LLDYQGML | 85 | HBV envelope 260-267 |
| LLVPFV | 86 | HBV envelope 338-343 |
| SILSPFMPLL | 87 | HBV envelope 370-379 |
| PLLPIFFCL | 88 | HBV envelope 377-385 |
| ILSTLPETTV | 89 | HBV core 529-538 |
| FLPSDFFPSV | 90 | HBV core 47-56 |
| KLHLYSHPI | 91 | HBV polymerase 489-498 |
| ALMPLYACI | 92 | HBV polymerase 642-651 |
| HLYSHPIIL | 93 | HBV polym. 1076-1084 |
| FLLSLGIHL | 94 | HBV polym. 1147-1153 |
| HLLVGSSGL | 95 | HBV polymerase 43-51 |
| GLSRYVARL | 96 | HBV polymerase 455-463 |
| LLAQFTSAI | 97 | HBV polymerase 527-535 |
| YMDDVVLGA | 98 | HBV polymerase 551-559 |
| GLYSSTVPV | 99 | HBV polymerase 61-69 |
| NLSWLSLDV | 100 | HBV polymerase 996-1004 |
| KLPQLCTEL | 101 | HPV 16 E6 18-26 |
| LQTTIHDII | 102 | HPV 16 E6 26-34 |
| FAFRDLCIV | 103 | HPV 16 E6 52-60 |
| YMLDLQPET | 104 | HPV 16 E7 11-19 |
| TLHEYMLDL | 105 | HPV 16 E7 7-15 |
| LLMGTLGIV | 106 | HPV 16 E7 82-90 |
| TLGIVCPI | 107 | HPV 16 E7 86-93 | polypeptide which, when expressed in a macrophage in vivo, downregulates an immune response. Examples of such polypeptides include tolerizing polypeptides, MHC blocking peptides, and cytokines.

In another embodiment, the invention features a process for preparing microparticles. A first solution, including a polymer dissolved in an organic solvent, is mixed (e.g., with sonication) with a second solution, which includes a nucleic acid dissolved or suspended in a polar or hydrophilic solvent. The mixture forms a first emulsion. The first emulsion is then mixed with a third solution which includes an organic compound, to form a second emulsion containing microparticles of polymer matrix and nucleic acid. The mixing steps can be executed, for example, in a homogenizer, vortex mixer, or sonicator. Both mixing steps are carried out in a manner that minimizes shearing of the nucleic acid while producing microparticles on average smaller than 100 microns in diameter.

The second emulsion is optionally mixed with a fourth solution including an organic solvent.

The procedure can include the additional step of washing the microparticles with an aqueous solution to remove organic solvent, thereby producing washed microparticles. The washed microparticles can then be subjected to a temperature below 0° C., to produce frozen microparticles, which are in turn lyophilized to produce lyophilized microparticles.

When desired, the procedure can include the additional step of screening the microparticles to remove those larger than 100 microns (or even 20 microns) in diameter.

Still another embodiment of the invention features a preparation of microparticles which include a polymeric matrix, a proteinaceous antigenic determinant or other protein (e.g., one which up- or down-regulates immune responses), and a DNA molecule which encodes an antigenic polypeptide that can be different from, or the same as, the aforementioned protein/antigenic determinant. The antigenic determinant contains an epitope which can elicit an antibody response. The antigenic polypeptide expressed from the DNA can induce a T cell response (e.g., a CTL response). The DNA can be plasmid DNA, and can be combined in the same microparticle as the protein/antigenic determinant, or the two can be in distinct microparticles which are then mixed together. In another embodiment, the invention features a method of administering nucleic acid to an animal by introducing into the animal (e.g., a mammal such as a human, non-human primate, horse, cow, pig, sheep, goat, dog, cat, mouse, rat, guinea pig, hamster, or ferret) any of the microparticles described in the paragraphs above. The microparticles can be provided suspended in a aqueous solution or any other suitable formulation, and can be, for example, injected or implanted (e.g., surgically) into the animal. They can optionally be delivered in conjunction with a protein such as a cytokine, an interferon, or an antigen.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1A:
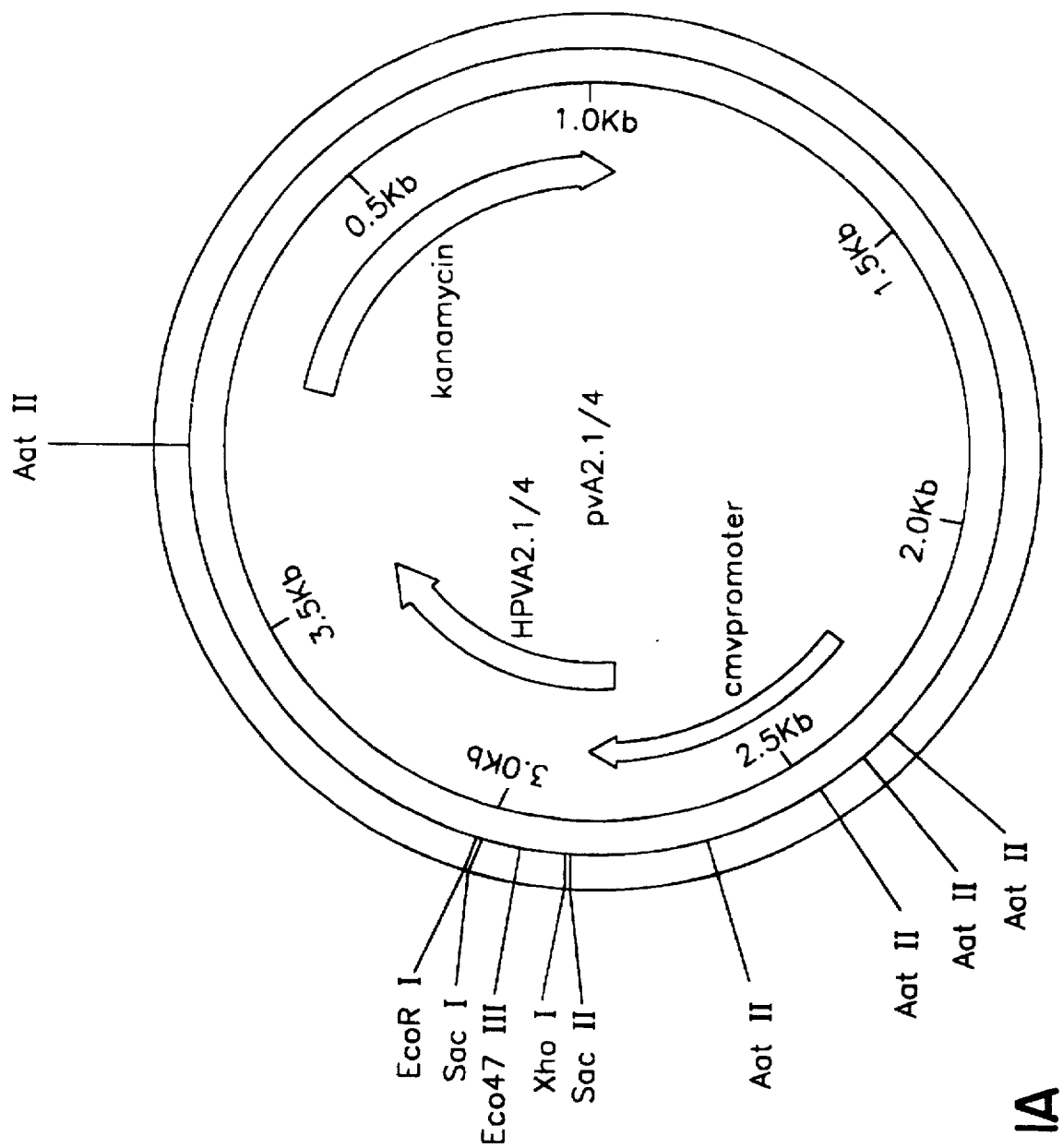
FIGS. 1A to 1C are a set of three plasmid maps, of the pvA2.1/4, luciferase, and VSV-Npep plasmids, respectively.

The microparticles of the invention are formulated in one of two ways: (1) to maximize delivery into the patient's phagocytic cells, or (2) to form a deposit in the tissues of the patient, from which the nucleic acid is released gradually over time; upon release from the microparticle, the nucleic acid is taken up by neighboring cells (including APCs) as free DNA. In both cases, maintaining the integrity of the DNA is a priority. For plasmid DNA, this means maximizing the percentage of plasmid molecules that are supercoiled and thus capable of more efficient transfection than non-supercoiled (i.e., nicked or linear) plasmids. Means for protecting the integrity of the nucleic acid include minimizing the shearing forces to which the nucleic acid is necessarily exposed in the process of microparticle formation, and limiting sonication times during preparation. For example, it is necessary to achieve a balance between sonication time and intensity. These techniques are discussed below.

Phagocytosis of microparticles by macrophages and other antigen presenting cells (APCs) is an effective means for introducing the nucleic acid into these cells. Phagocytosis by these cells can be increased by maintaining a particle size below about 20 µm, and preferably below about 11 µm. The type of polymer used in the microparticle can also affect the efficiency of uptake by phagocytic cells, as discussed below.

The microparticles can be delivered directly into the bloodstream (i.e., by intravenous or intraarterial injection or infusion) if uptake by the phagocytic cells of the reticuloendothelial system (RES) is desired. Alternatively, one can target, via subcutaneous injection, take-up by the phagocytic cells of the draining lymph nodes. The microparticles can also be introduced intradermally (i.e., to the APCs of the skin, such as dendritic cells and Langerhans cells). Another useful route of delivery (particularly for DNAs encoding tolerance-inducing polypeptides) is via the gastrointestinal tract, e.g., orally. Finally, the microparticles can be introduced into the lung (e.g., by inhalation of powdered microparticles or of a nebulized or aerosolized solution containing the microparticles), where the particles are picked up by the alveolar macrophages.

Once a phagocytic cell phagocytoses the microparticle, the nucleic acid is released into the interior of the cell. Upon release, it can perform its intended function: for example, expression by normal cellular transcription/translation machinery (for an expression vector), or alteration of cellular processes (for antisense or ribozyme molecules).

Because these microparticles are passively targeted to macrophages and other types of phagocytic cells, they represent a means for modulating immune function. Macrophages serve as professional APCs, expressing both MHC class I and class II molecules. Delivery, via microparticles, of an expression vector encoding a foreign antigen which binds to an MHC class I or class II molecule will induce a host T cell response against the antigen, thereby conferring host immunity.

Where the expression vector encodes a blocking peptide (See, e.g., WO 94/04171) that binds to an MHC class it II molecule involved in autoimmunity, presentation of the autoimmune disease-associated self peptide by the class II molecule is prevented, and the symptoms of the autoimmune disease alleviated.

In another example, an MHC binding peptide that is identical or almost identical to an autoimmunity-inducing peptide can affect T cell function by tolerizing or anergizing the T cell. Alternatively, the peptide could be designed to modulate T cell function by altering cytokine secretion profiles following recognition of the MHC/peptide complex. Peptides recognized by T cells can induce secretion of cytokines that cause B cells to produce antibodies of a particular class, induce inflammation, and further promote host T cell responses.

Induction of immune responses can require several factors. It is this multifactorial nature that provides impetus for attempts to manipulate immune related cells on multiple fronts, using the microparticles of the invention. For example, microparticles can be prepared which carry both DNA and polypeptides within each microparticle. Alternatively, a mixture of microparticles can be used, some of which contain DNA and the rest of which contain polypeptide. These dual-function microparticle preparations are discussed below.

CTL Responses

Class I molecules present antigenic peptides to immature T cells. In order to fully activate T cells, factors in addition to the antigenic peptide are required. Non-specific proteins, such as interleukin-2 (IL-2), IL-12, and gamma interferon (γ-IFN), promote CTL responses and can be provided together with DNA encoding polypeptides which include CTL epitopes. Alternatively, proteins which bear helper T ($T_H$) determinants can be included with DNA encoding the CTL epitope. $T_H$ epitopes promote secretion of cytokines from $T_H$ cells and play a role in the differentiation of nascent T cells into CTLs.

Alternatively, proteins which promote migration of lymphocytes and macrophages to a particular area could be included in microparticles along with appropriate DNA molecules. Uptake of the DNA is enhanced as a result, because release of the protein would cause an influx of phagocytic cells and T cells as the microparticle degrades. The macrophages would phagocytose the remaining microparticles and act as APC, and the T cells would become effector cells.

Antibody Responses

Elimination of certain infectious agents from the host may require both antibody and CTL responses. For example, when the influenza virus enters a host, antibodies can often prevent it from infecting host cells. However, if cells are infected, then a CTL response is required to eliminate the infected cells and to prevent the continued production of virus within the host.

In general, antibody responses are directed against conformational determinants and thus require the presence of a protein or a protein fragment containing such a determinant. In contrast, T cell epitopes are linear determinants, typically just 7–25 residues in length. Thus, when there is a need to induce both a CTL and an antibody response, the microparticles can include both an antigenic protein and the DNA encoding a CTL epitope.

Slow release of the protein from microparticles would lead to B cell recognition and subsequent secretion of antibody. In contrast, phagocytosis of the microparticles would cause APCs (1) to express the DNA of interest, thereby generating a T cell response; and (2) to digest the protein released from the microparticles, thereby generating peptides which are subsequently presented by class II molecules. Presentation by class II molecules promotes both antibody and CTL responses, since $T_H$ cells activated by the class II/peptide complexes would secrete non-specific cytokines.

Immunosuppression

Certain immune responses lead to allergy and autoimmunity, and so can be deleterious to the host. In these instances, there is a need to inactivate tissue-damaging immune cells. Immunosuppression can be achieved with microparticles bearing DNA which encodes epitopes that down regulate $T_H$ cells and CTLs (e.g., "blocking" peptides). In these microparticles, the effect of the immunosuppressive DNA could be amplified by including certain proteins in the carrier microparticles with the DNA. A list of such proteins includes antibodies, receptors, and the interleukins.

For example, antibodies to stimulatory cytokines or homing proteins, such as integrins or intercellular adhesion molecules (ICAMs), can increase the efficacy of the immunosuppressive DNA epitope. These proteins serve to inhibit the responses of already-activated T cells, while the DNA further prevents activation of nascent T cells. Induction of T cell regulatory responses can be influenced by the cytokine milieu present when the T cell receptor (TCR) is engaged. Cytokines such as IL-4, IL-10, and IL-6 promote $T_H2$ differentiation in response to the DNA-encoded epitope. $T_H2$ responses can inhibit the formation of $T_H1$ cells and the corresponding deleterious responses which result in the pathologies of rheumatoid arthritis, multiple sclerosis and juvenile diabetes.

Inclusion of proteins comprising soluble forms of costimulatory molecules (e.g., CD-40, gp-39, B7-1, and B7-2) is another way to inhibit activation of particular T cell and/or B cells responses. For example, B7-1 is involved in the activation of $T_H1$ cells, and B7-2 activates $T_H{}^2$ cells. Depending on the response that is required, one or the other of these proteins could be included in the microparticle with the DNA, or could be supplied in separate microparticles mixed with the DNA-containing microparticles Microparticles containing just proteins can be prepared by standard methods; preparation of microparticles containing both protein and DNA is discussed below.

Microparticles for Implantation

A second microparticle formulation of the invention is intended not to be taken up directly by cells, but rather to serve primarily as a slow-release reservoir of nucleic acid that is taken up by cells only upon release from the microparticle through biodegradation. The polymeric particles in this embodiment should therefore be large enough to preclude phagocytosis (i.e., larger than 10 μm and preferably larger than 20 μm). Such particles are produced by the methods described above for making the smaller particles, but with less vigorous mixing of the aforementioned first or second emulsions. That is to say, a lower homogenization speed, vortex mixing speed, or sonication setting can be used to obtain particles having a diameter around 100 μm rather than 10 μm. The time of mixing also can be altered.

The larger microparticles can be formulated as a suspension, a powder, or an implantable solid, to be delivered by intramuscular, subcutaneous, intradermal, intravenous, or intraperitoneal injection; via inhalation (intranasal or intrapulmonary); orally; or by implantation. These particles are useful for delivery of any expression vector or other nucleic acid for which slow release over a relatively long term is desired: e.g., an antisense molecule, a gene replacement therapeutic, a means of delivering cytokine-based, antigen-based, or hormone-based therapeutic, or an immunosuppressive agent. The rate of degradation, and consequently of release, varies with the polymeric formulation. This parameter can be used to control immune function. For example, one would want a relatively slow release of antigen to elicit secretion of IL-4 or IL-10, and a relatively rapid release of antigen to elicit secretion of IL-2 or γ-IFN.

Composition of Polymeric Particles

Polymeric material is obtained from commercial sources or can be prepared by known methods. For example, polymers of lactic and glycolic acid can be generated as described in U.S. Pat. No. 4,293,539 or purchased from Aldrich.

Alternatively, or in addition, the polymeric matrix can include polylactide, polyglycolide, poly(lactide-co-glycolide), polyanhydride, polyorthoester, polycaprolactone, polyphosphazene, proteinaceous polymer, polypeptide, polyester, or polyorthoester.

Preferred controlled release substances which are useful in the formulations of the invention include the polyanhydrides, co-polymers of lactic acid and glycolic acid wherein the weight ratio of lactic acid to glycolic acid is no more than 4:1, and polyorthoesters containing a degradation-enhancing catalyst, such as an anhydride, e.g., 1% maleic anhydride. Since polylactic acid takes at least one year to degrade in vivo, this polymer should be utilized by itself only in circumstances where such a degradation rate is desirable.

Association of Nucleic Acid and Polymeric Particles

Polymeric particles containing nucleic acids are made using a double emulsion technique. First, the polymer is dissolved in an organic solvent. A preferred polymer is polylactic-co-glycolic acid (PLGA), with a lactic/glycolic acid weight ratio of 65:35, 50:50, or 75:25. Next, a sample of nucleic acid suspended in aqueous solution is added to the polymer solution and the two solutions are mixed to form a first emulsion. The solutions can be mixed by vortexing or shaking, and in a preferred method, the mixture can be sonicated. Most preferable is any method by which the nucleic acid receives the least amount of damage in the form of nicking, shearing, or degradation, while still allowing the formation of an appropriate emulsion. For example, acceptable results can be obtained with a Vibra-cell model VC-250 sonicator with a ⅛" microtip probe, at setting #3.

During this process, the polymer forms into minute "microparticles," each of which contains some of the nucleic acid-containing solution. If desired, one can isolate a small amount of the nucleic acid at this point in order to assess integrity, e.g., by gel electrophoresis.

The first emulsion is then added to an organic solution. The solution can be comprised of, for example, methylene chloride, ethyl acetate, or acetone, preferably containing polyvinyl alcohol (PVA), and most preferably having a 1:100 ratio of the weight of PVA to the volume of the solution. The first emulsion is generally added to the organic solution with stirring in a homogenizer or sonicator. For example, one can use a Silverson Model L4RT homogenizer (⅝" probe) set at 7000 RPM for about 12 seconds. A 60 second homogenization time would be too harsh at this homogenization speed.

This process forms a second emulsion which is subsequently added to another organic solution with stirring (e.g., in a homogenizer). In a preferred method, the latter solution is 0.05% w/v PVA. The resultant microparticles are washed several times with water to remove the organic compounds. Particles can be passed through sizing screens to selectively remove those larger than the desired size. If the size of the microparticles is not crucial, one can dispense with the sizing step. After washing, the particles can either be used immediately or be lyophilized for storage.

Larger particles, such as those used for implantation, can be obtained by using less vigorous emulsification conditions when making the first emulsion, as has already been described above at length. For example, larger particles could be obtained with the Silverson homogenizer set at 5000 RPM for about 12 seconds.

Characterization of Microparticles

The size distribution of the microparticles prepared by the above method can be determined with a COULTERM™ counter. This instrument provides a size distribution profile and statistical analysis of the particles. Alternatively, the average size of the particles can be determined by visualization under a microscope fitted with a sizing slide or eyepiece.

If desired, the nucleic acid can be extracted from the microparticles for analysis by the following procedure. Microparticles are dissolved in an organic solvent such as chloroform or methylene chloride in the presence of an aqueous solution. The polymer stays in the organic phase, while the DNA goes to the aqueous phase. The interface between the phases can be made more distinct by centrifugation. Isolation of the aqueous phase allows recovery of the nucleic acid. To test for degradation, the extracted nucleic acid can be analyzed by HPLC or gel electrophoresis.

To increase the recovery of nucleic acid, additional organic solvents, such as phenol and chloroform, can be added to the dissolved microparticles, prior to the addition of the aqueous solution. Following addition of the aqueous solution, the nucleic acid enters the aqueous phase, which can easily be partitioned from the organic phase after mixing. For a clean interface between the organic and aqueous phases, the samples should be centrifuged. The nucleic acid is retrieved from the aqueous phase by precipitation with salt and ethanol in accordance with standard methods.

Intracellular Delivery of Microparticles

Microparticles containing DNA are resuspended in saline, buffered salt solution, or tissue culture medium. For in vitro/ex vivo use, the suspension of microparticles can be added either to cultured adherent mammalian cells or to a cell suspension. Following a 1–24 hour period of incubation, those particles not taken up are removed by aspiration or centrifugation over fetal calf serum. The cells can be either analyzed immediately or recultured for future analysis.

Uptake of microparticles containing nucleic acid into the cells can be detected by PCR, or by assaying for expression of the nucleic acid. For example, one could measure transcription of the nucleic acid with a Northern blot, reverse transcriptase PCR, or RNA mapping. Protein expression can be measured with an appropriate antibody-based assay, or with a functional assay tailored to the function of the polypeptide encoded by the nucleic acid. For example, cells expressing a nucleic acid encoding luciferase can be assayed as follows: after lysis in the appropriate buffer (e.g., cell lysis culture reagent, Promega Corp, Madison Wis.), the lysate is added to a luciferin containing substrate (Promega Corp) and the light output is measured in a luminometer or scintillation counter. Light output is directly proportional to the expression of the luciferase gene.

If the nucleic acid encodes a peptide known to interact with a class I or class II MHC molecule, an antibody specific for that MHC molecule/peptide complex can be used to detect the complex on the cell surface of the cell, using a fluorescence activated cell sorter (FACS). Such antibodies can be made using standard techniques (Murphy et al. Nature, Vol. 338, 1989, pp. 765–767). Following incubation with microparticles containing a nucleic acid encoding the peptide, cells are incubated for 10–120 minutes with the specific antibody in tissue culture medium. Excess antibody is removed by washing the cells in the medium. A fluorescently tagged secondary antibody, which binds to the first antibody, is incubated with the cells. These secondary antibodies are often commercially available, or can be prepared using known methods. Excess secondary antibody must be washed off prior to FACS analysis.

One can also assay by looking at T or B effector cells. For example, T cell proliferation, cytotoxic activity, or cytokine secretion can be measured.

Alternatively, one can directly demonstrate intracellular delivery of the particles by using nucleic acids which are fluorescently labeled, and analyzing the cells by FACS.

Internalization of the fluorescently labeled nucleic acid causes the cell to fluoresce above background levels. Because it is rapid and quantitative, FACS is especially useful for optimization of the conditions for in vitro or in vivo delivery of nucleic acids. Following such optimization, use of the fluorescent label is discontinued.

If the nucleic acid itself directly affects cellular function, e.g., if it is a ribozyme or an antisense molecule, or is transcribed into one, an appropriate functional assay can be utilized. For example, if the ribozyme or antisense nucleic acid is designed to decrease expression of a particular cellular protein, the expression of that protein can be monitored.

In Vivo Delivery of Microparticles

Microparticles containing nucleic acid can be injected into mammals intramuscularly, intravenously, intraarterially, intradermally, intraperitoneally, or subcutaneously, or they can be introduced into the gastrointestinal tract or the respiratory tract, e.g., by inhalation of a solution or powder containing the microparticles. Expression of the nucleic acid is monitored by an appropriate method. For example, expression of a nucleic acid encoding an immunogenic protein of interest is assayed by looking for an antibody or T cell response to the protein.

Antibody responses can be measured by testing serum in an ELISA assay. In this assay, the protein of interest is coated onto a 96 well plate and serial dilutions of serum from the test subject are pipetted into each well. A secondary, enzyme-linked antibody, such as anti-human, horseradish peroxidase-linked antibody, is then added to the wells. If antibodies to the protein of interest are present in the test subject's serum, they will bind to the protein fixed on the plate, and will in turn be bound by the secondary antibody. A substrate for the enzyme is added to the mixture and a colorimetric change is quantitated in an ELISA plate reader. A positive serum response indicates that the immunogenic protein encoded by the microparticle's DNA was expressed in the test subject, and stimulated an antibody response. Alternatively, an ELISA spot assay can be employed in order to look at B cells specifically.

T cell proliferation in response to a protein following intracellular delivery of microparticles containing nucleic acid encoding the protein is measured by assaying the T cells present in the spleen, lymph nodes, or peripheral blood lymphocytes of a test animal. The T cells obtained from such a source are incubated with syngeneic APCs in the presence of the protein or peptide of interest. Proliferation of T cells is monitored by uptake of $^3$H-thymidine, according to standard methods. The amount of radioactivity incorporated into the cells is directly related to the intensity of the proliferative response induced in the test subject by expression of the microparticle-delivered nucleic acid. A positive response indicates that the microparticle containing DNA encoding the protein or peptide was taken up and expressed by APCs in vivo.

The generation of cytotoxic T cells can be demonstrated in a standard $^{51}$Cr release assay. In these assays, spleen cells or peripheral blood lymphocytes obtained from the test subject are cultured in the presence of syngeneic APCs and either the protein of interest or an epitope derived from this protein. After a period of 4–6 days, the effector cytotoxic T cells are mixed with $^{51}$Cr-labeled target cells expressing an epitope derived from the protein of interest. If the test subject raised a cytotoxic T cell response to the protein or peptide encoded by the nucleic acid contained within the microparticle, the cytotoxic T cells will lyse the targets. Lysed targets will release the radioactive $^{51}$Cr into the medium. Aliquots of the medium are assayed for radioactivity in a scintillation counter. Assays, such as ELISA, can also be used to measure cytokine profiles.

The following are examples of the practice of the invention. They are not to be construed as limiting the scope of the invention in any way.

EXAMPLE 1

Incorporation of DNA; Analysis of Particle Size and DNA Integrity

Preparation of DNA for Incorporation

Figure 1B:
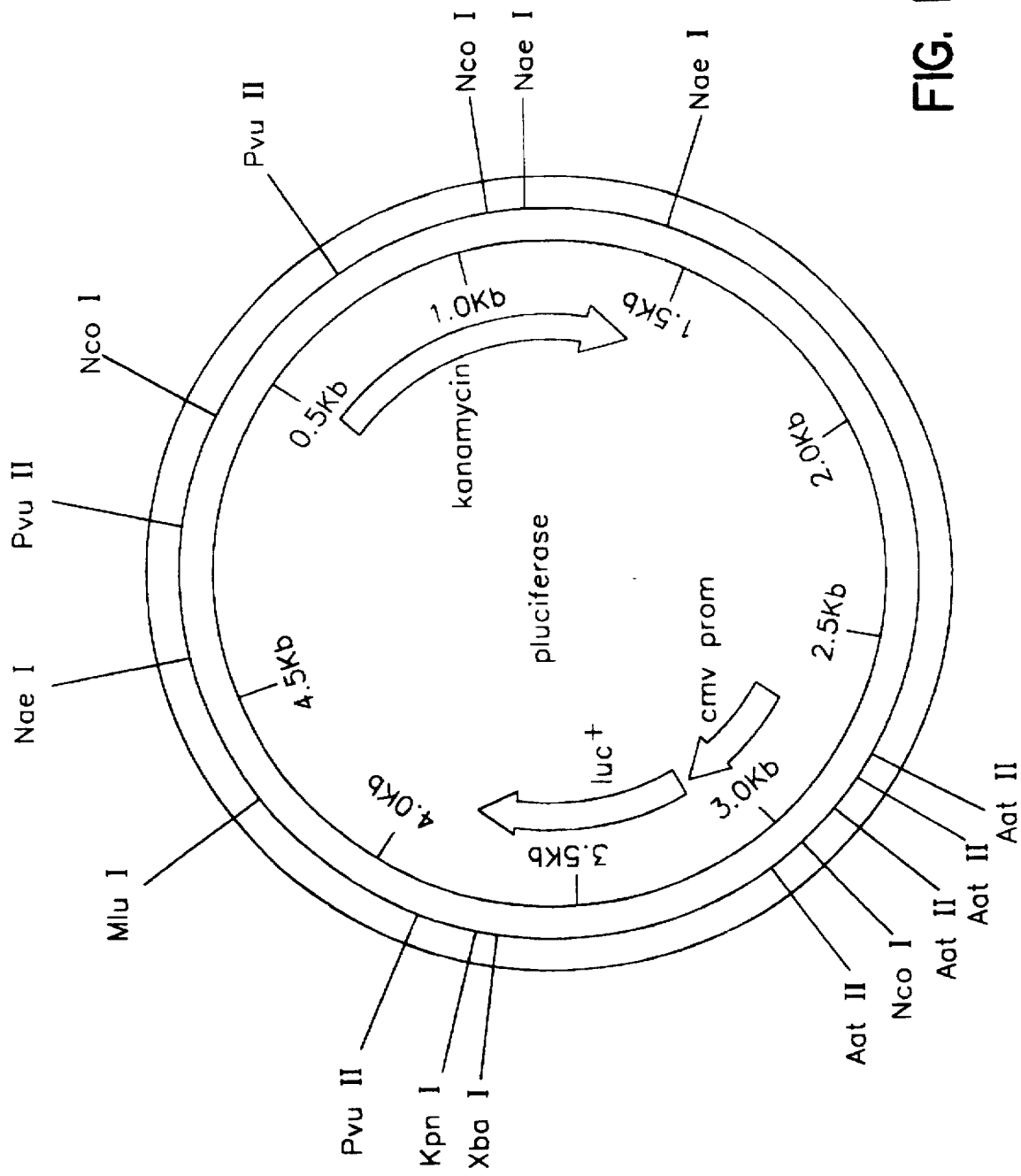
Figure 1C:
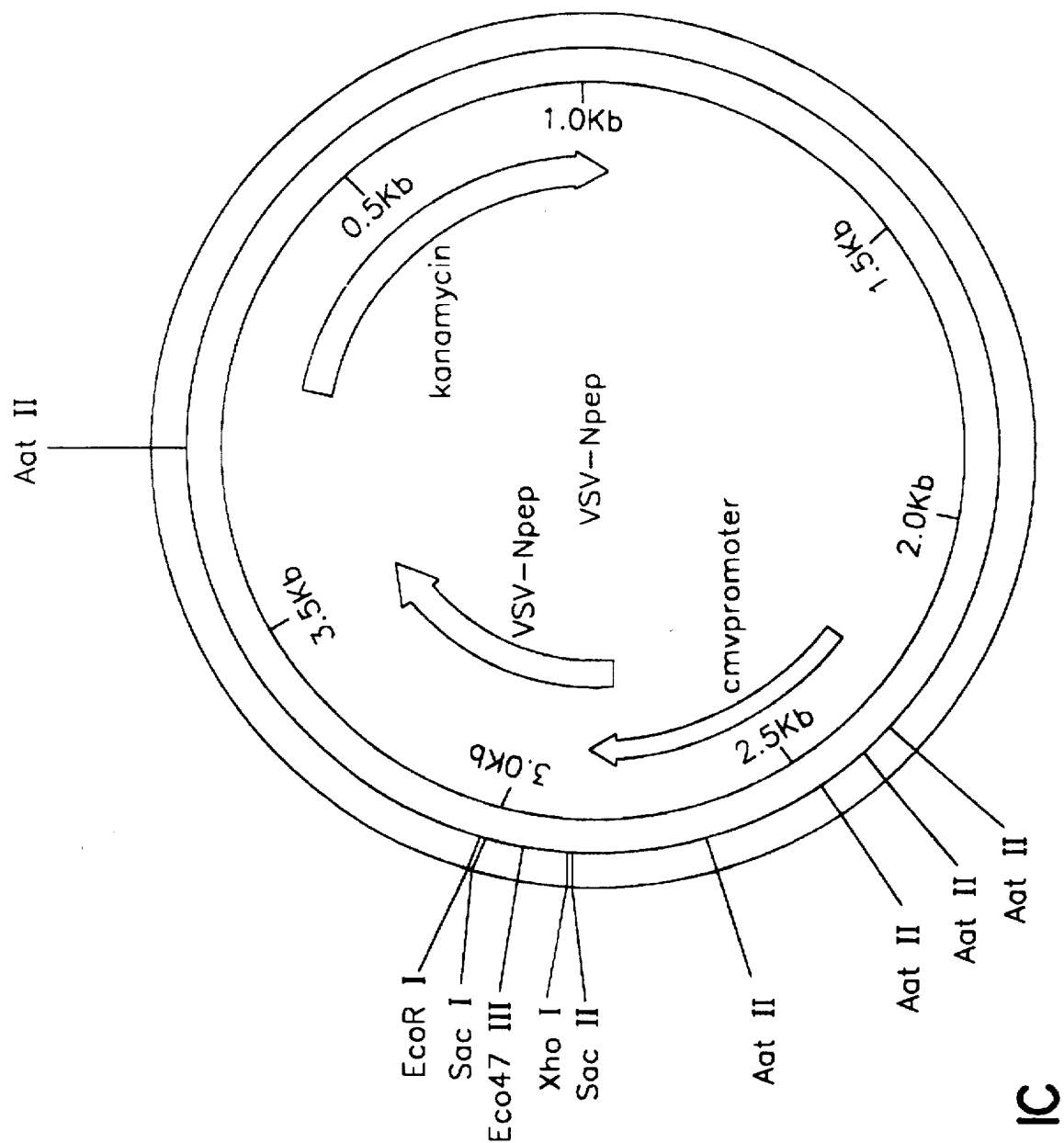

Plasmid DNA was prepared by standard methods using MEGA-PREP™ Kit (Qiagen) according to the manufacturer's instructions. An endotoxin-free buffer kit (Qiagen) was used for all DNA manipulations. The DNA was resuspended in distilled, deionized, sterile water to give a final concentration of 3 µg/µl. FIG. 1 shows plasmid maps of DNA expression vectors encoding a) luciferase, b) a vesicular stomatitis virus (VSV) peptide epitope termed VSV-Npep, and c) a human papilloma virus (HPV) peptide epitope termed A2.1/4.

Association of DNA with PLGA 200 mg of poly-lactic-co-glycolic acid (PLGA) (Medisorb, 65:35 ratio of lactic acid to glycolic acid) was dissolved in 5–7 ml of methylene chloride. 300 µl of the DNA solution prepared above, containing 900 µg DNA, was added to the PLGA solution. The mixture was sonicated in a Vibra-cell model VC-250 sonicator with a ⅛" microtip probe, on setting #3 for 5–60 seconds, and the resulting emulsion was analyzed. An emulsion verified to contain particles of desired size having DNA of satisfactory integrity (as determined below) was added to a beaker containing 50 ml aqueous 1% w/v polyvinyl alcohol (PVA) (mw range: 30–70 kdal). The mixture was homogenized in a Silverson homogenizer set at 3000–9000 RPM for 5–60 seconds. Again, the DNA integrity was analyzed. In the cases where the DNA was found to be sufficiently intact, the resulting second emulsion was transferred into a second beaker containing 100 ml aqueous 0.05% PVA, with constant stirring. The stirring was continued for 2–3 hours.

The microparticle solution was poured into a 250 ml centrifuge tube and spun at 2000 rpm for 10 minutes. The contents of the tubes were decanted and the sedimented particles were resuspended in 100 ml deionized water. After repeating the centrifugation and decanting steps, the particles were frozen in liquid nitrogen and finally lyophilized until dry.

Figure 2:
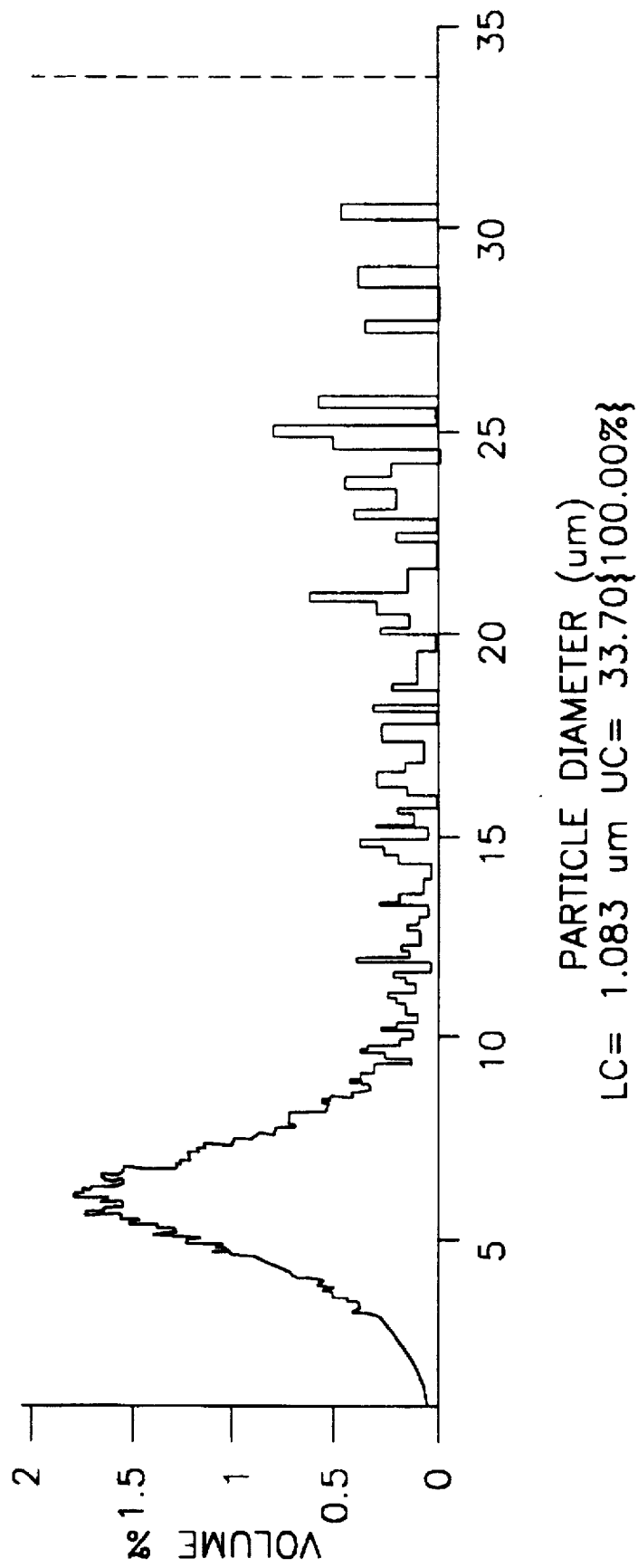
FIG. 2 is a plot of size distribution of DNA-containing microparticles as analyzed on a COULTER™ counter.

Analysis of Microparticle Size Profile 5 mg of the lyophilized microparticles were resuspended in 200 µl water. The resulting suspension was diluted to about 1:10,000 for analysis with a COULTER™ counter. FIG. 2 is a print-out from the COULTER™ counter which indicates that approximately 85% of the microparticles were between 1.1 and 10 µm in diameter.

Determination of DNA Integrity

2–5 µg of the microparticles were wet with 10 µl water in an EPPENDORF™ tube. 500 µl chloroform was added with thorough mixing to dissolve the polymeric matrix. 500 µl water was added, again with mixing. The resulting emulsion was centrifuged at 14,000 rpm for 5 minutes. The aqueous layer was transferred to a clean EPPENDORF™ tube, along with 2 volume equivalents of ethanol and 0.1 volume equivalents of 3M aqueous sodium acetate. The mixture was centrifuged at 14,000 rpm for 10 minutes. After aspiration of the supernatant, the pelleted DNA was resuspended in 50 µl water. 5 µg DNA was electrophoresed on a 0.8% agarose gel next to a standard containing the input DNA. The DNA on the gel was visualized on a UV light box. Comparison with the standard gives an indication of the integrity of the microparticles' DNA. The microparticle formation procedure was deemed successful if the incorporated DNA retained a high percentage of supercoiled DNA relative to the input DNA.

Figure 3A:
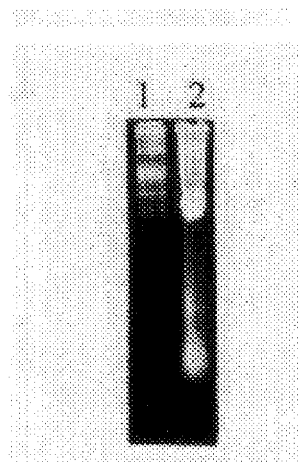
FIGS. 3A and 3B are a set of photographs of two agarose electrophoresis gels indicating degree of DNA supercoiling as a function of different homogenization speeds and durations.
Figure 3B:
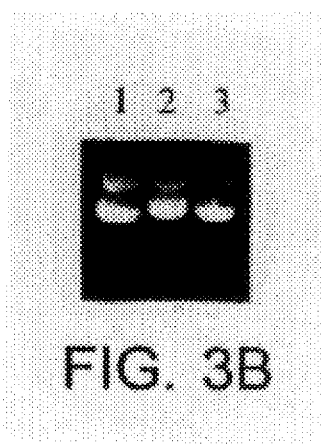

As indicated in FIGS. 3A and 3B, homogenization speed and duration are inversely related to DNA integrity. FIG. 3A depicts the DNA isolated from microparticles prepared by homogenization at 7000 rpm for 1 minute (lane 1), and supercoiled input DNA (lane 2). FIG. 3B shows DNA isolated from microparticles prepared by homogenization at 7000 rpm for 5 seconds (lane 1), DNA isolated from microparticles prepared by homogenization at 5000 rpm for 1 minute (lane 2), and supercoiled input DNA (lane 3).

EXAMPLE 2
In Vitro Cell Studies
In Vitro Phagocytosis of DNA-Containing Microparticles Into each of two wells of a six-well tissue culture dish, about $10^6$ macrophages were plated in 3 ml RPMI medium containing 10% fetal calf serum. 5 mg of the microparticles containing DNA encoding luciferase were resuspended in 200 µl saline solution, and 50 µl of the resulting suspension was added to one of the wells containing macrophages. The plate was incubated at 37° C. for 1–6 hours. Side vs. forward scatter (i.e., intracellular complexity vs. size) of the cells was analyzed by FACS using a Becton Dickinson FACS instrument.

Figure 4A:
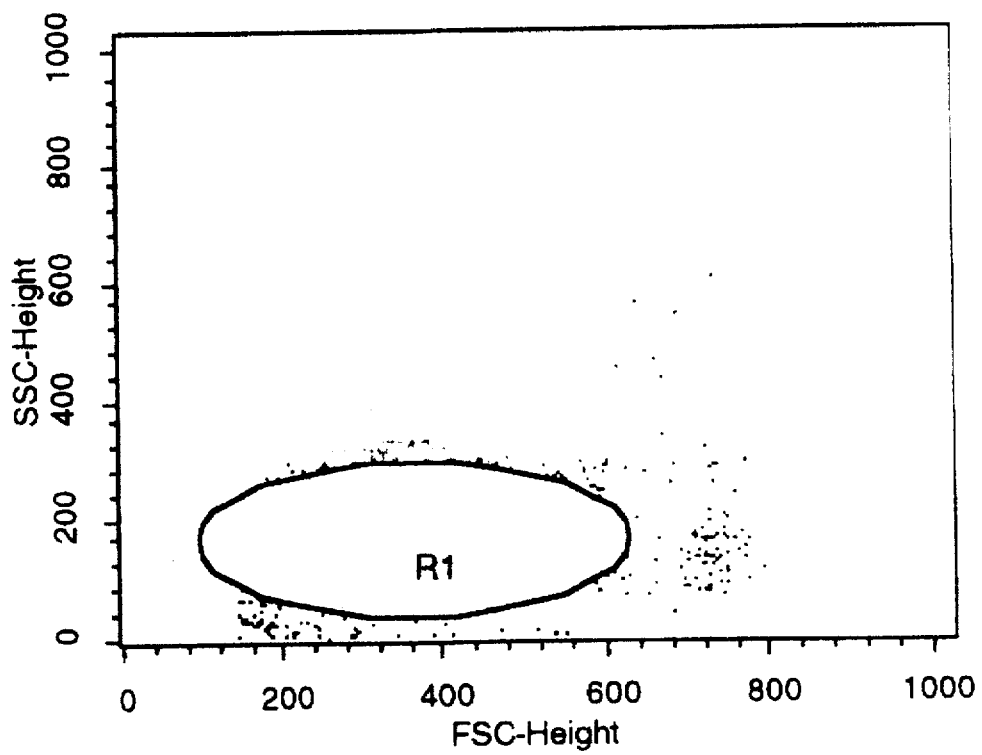
FIGS. 4A and 4B are a pair of FACS printouts comparing cell populations in the absence or presence of microparticles.
Figure 4B:
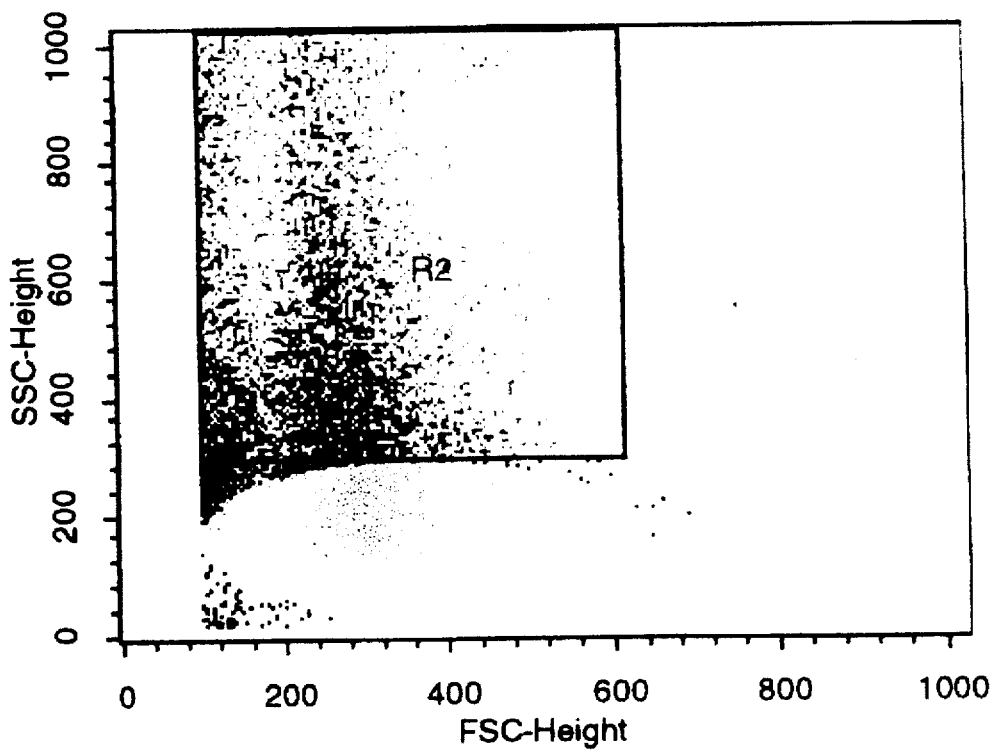

FIG. 4 shows the results. Cell populations that have not phagocytosed are found in region R1. Phagocytosing cells remain the same size (FSC profile), but demonstrate an increased side scatter profile. These cells are found in region R2.

Measurement of DNA Expression Following Phagocytosis

Into two wells of a 24-well tissue culture dish, about $2.5\times10^5$ macrophages were plated in 1 ml RPMI medium containing 10% fetal calf serum. The plate was incubated at 37° C. for 6 hours. 1 mg of the lyophilized microparticles containing DNA encoding luciferase was resuspended in 400 µl saline solution. 6 µl of the resulting suspension was added to one of the wells containing macrophages, and 25 µl of suspension was added to the other. The plate was incubated at 37° C. for 4 hours. The medium, including the microparticles, was removed and fresh medium added to the cells. The plate was again incubated at 37° C. for 1–5 days. The cells were harvested into a tube and spun at 1,500 RPM for 5 minutes. The pelleted cells were resuspended in 100 µl of 1× Cell Lysis Buffer (Promega) in an EPPENDORF™ tube. The mixture was centrifuged at 14,000 RPM for 5 minutes in order to precipitate out any cell debris. The cell lysate was assayed by adding 5 µl of the supernatant to 100 µl of luciferase substrate (Promega) and measuring the light output on a TOPCOUNT™ combination luminometer/ scintillation counter (Packard Instruments).

The data for this experiment are provided in Table 5. They indicate that cells phagocytosing microparticles that contain, for example, luciferase DNA, do in fact express the DNA. Thus, DNA integrity and functionality are confirmed. The data also indicate that the uptake of the microparticles by phagocytosis does not prevent the DNA from reaching the nucleus.

TABLE 5

Phagocytosis of encapsulated DNA leads to expression of a luciferase reporter gene construct.
MICROPARTICLES CONTAINING:

| | Luciferase DNA | | Control DNA | |
|---|---|---|---|---|
| | 25 µl | 6 µl | 25 µl | 6 µl |
| Day 1 | 1257 | 168 | 103 | 245 |
| Day 2 | 2632 | 492 | 107 | 133 |
| Day 3 | 3400 | 507 | 80 | 93 |
| Day 5 | 763 | 310 | 90 | 90 |

Data given in counts per 0.01 minute

EXAMPLE 3
In Vivo Cell Studies
In Vivo Expression of Incorporated DNA 45 mg of luciferase cDNA in microparticles was resuspended in 250 µl saline solution. 40 µl of the resulting suspension was injected into each tibialis anterior muscle of a mouse. Seven days later, each tibialis anterior was dissected and placed in an EPPENDORF™ tube on dry ice. Using a mortar and pestle cooled with dry ice, each tibialis anterior muscle was ground into a powder, then return to the EPPENDORF™ tube. 500 µl 1× cell lysis buffer (Promega) was added. The tube was shaken upside-down on a vortex mixer at 40° C. for 15 minutes. The tube and its contents were frozen in liquid nitrogen, then thawed to 37° C. The freeze/thaw cycle was repeated two more times. The tube was centrifuged 14,000 RPM for 10 minutes. The supernatant was transferred to a new tube and centrifuged again for 5 minutes. To assay for expression, 20 µl of the supernatant was added to 100 µl of luciferase substrate (Promega) and the light output was measured on a TOPCOUNT™ combination luminometer/scintillation counter (Packard Instruments).

The data for this experiment are provided in Table 6. They indicate that muscle cells can express DNA released from microparticles. Since these cells are not known to phagocytose, this is an example of depot effect.

TABLE 6

Expression of encapsulated luciferase DNA in murine muscles

| Muscle 1 | $2 \times 10^5$ |
|---|---|
| Muscle 2 | $8 \times 10^4$ |
| Muscle 3 | $1 \times 10^6$ |
| Muscle 4 | $6 \times 10^5$ |
| Control | $2 \times 10^2$ |

Data given in counts per 0.01 minute

Generation of Cytotoxic T Cells Following Injection of Microparticles Containing DNA 90 mg of microparticles containing DNA encoding VSV-Npep was resuspended in 900 µl of saline solution. 60 mg of microparticles containing control vector DNA was resuspended in 600 µl of saline solution. 300 µg VSV-Npep plasmid DNA was resuspended in 300 µl of saline solution. 300 µg control vector DNA was resuspended in 300 µl of saline solution. 150 µg of the VSV-N peptide was resuspended in incomplete Freund's adjuvant (IFA).

The five suspensions were injected intraperitoneally, intramuscularly, or subcutaneously, according to the following regimen:

1. Intraperitoneal: A first group of 3 mice was injected intraperitoneally with 100 µl of microparticles containing VSV-Npep DNA (Group 1). A second group of 3 mice was injected with 100 µl of microparticles containing control vector DNA (Group 2).

2. Intramuscular: (into each tibialis anterior muscle): A third group of 3 mice was injected intramuscularly with 100 µl of microparticles containing VSV-Npep DNA (Group 3). A fourth group of 3 mice was injected with 100 µl microparticles containing control vector DNA (Group 4). A fifth group of 3 mice was injected with 50 µg/leg VSV-Npep plasmid DNA (i.e., in the absence of microparticles) (Group 5). A sixth group of 3 mice was injected with 50 µg/leg control vector plasmid DNA (Group 6). 3. Subcutaneous: A seventh group of 3 mice was injected subcutaneously with 100 µl of microparticles containing VSV-Npep DNA (Group 7). An eighth group of 3 mice was injected with 50 µg VSV-N peptide/IFA (Group 8).

After two weeks, groups 5, 6, and 8, which received either synthetic peptide or DNA without microparticles, were injected again. Groups 1–4 and 7, which initially received microparticles, were not reinjected.

Seven days after the last set of injections, the murine spleens were harvested. Single cell suspensions were generated by standard methods, the red blood cells were lysed, and the remaining cells were resuspended in RPMI with 10% fetal calf serum to give a final concentration of $4 \times 10^6$ effector cells/ml. Half of the cells from each group were then incubated at 37° C. for 6 days with an equal number of peptide-pulsed syngeneic stimulator cells which had been previously treated with mitomycin C. The remaining cells were incubated with 50 µM peptide alone.

After the second day of incubation, 0.1 volume equivalents of IL-2-containing supernatant, derived from cells incubated in ConA, was added. After the sixth day of incubation, the effector cells were harvested and incubated in 96-well round-bottom plates containing $^{51}$Cr-labeled, peptide-pulsed target cells at 37° C. for 5 hours. The effector-to-target ratios for the wells ranged from 200:1 down to 1:1.

To determine the level of maximal lysis, 20 µl of aqueous 10% sodium dodecyl sulfate (SDS) was added to certain wells containing only target cells. To determine the level of spontaneous lysis, certain wells were incubated with media alone (i.e., target cells but no effector cells). Specific lysis is calculated as follows: [(experimental lysis)-(spontaneous lysis)/(maximal lysis)-(spontaneous lysis)]×100=specific lysis.

The results are shown in FIGS. 5–9.

Figure 5:
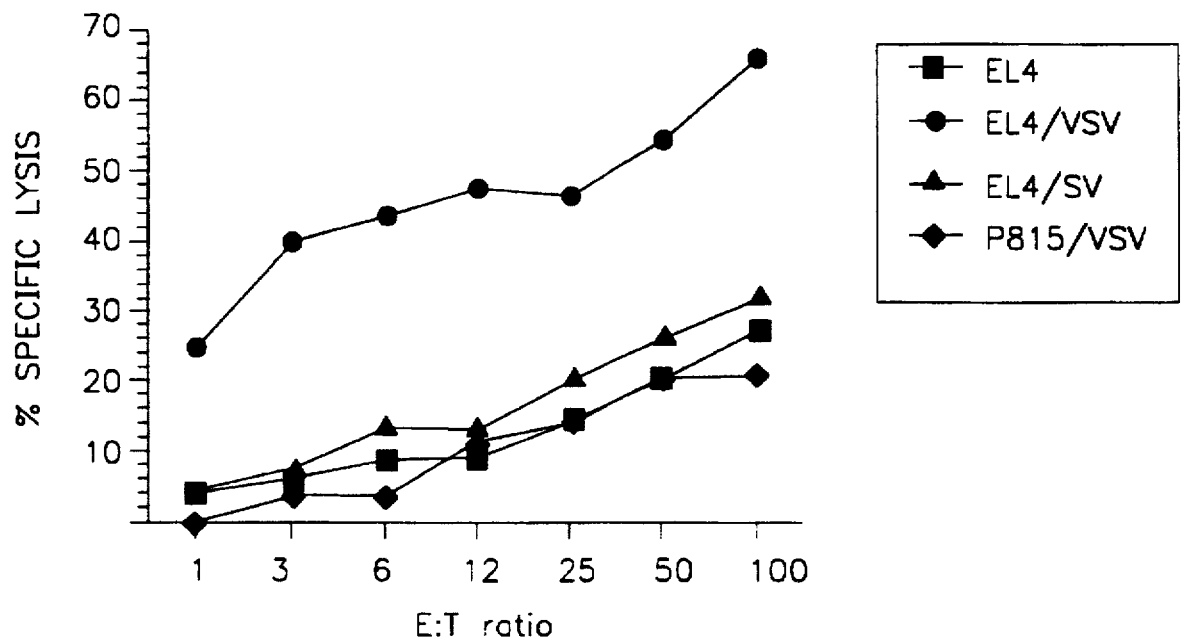
FIGS. 5 to 9 are plots of specific lysis vs. effector:target ratio.

In the experiment associated with FIG. 5, effector cells from mice (Group 1) immunized intraperitoneally with microparticles containing DNA that encodes a peptide from the VSV-N protein were tested for cytolytic activity against various target cells. The VSV peptide binds to the mouse H-2K$^b$ class I receptor. Syngeneic targets express the H-2K$^b$ receptor while the allogeneic targets used in this experiment express the H-2K$^d$ receptor.

CTL activity was tested on syngeneic targets (EL4) without peptide, syngeneic targets (EL4/VSV) labeled with the VSV peptide, syngeneic targets (EL4/SV) labeled with SV peptide (i.e., a non-specific peptide), and allogenic targets (P815/VSV) labeled with VSV peptide.

Because the allogeneic targets (P815/VSV) do not express the H-2K$^b$ receptor, they should not be recognized and lysed by the effector cells. Thus, P815 targets mixed with the VSV peptide are not lysed. Syngeneic targets (EL4) that do not have the VSV peptide are also not lysed. Syngeneic targets (EL4/SV) that express a peptide different from VSV are also not lysed. Only those targets (EL4/VSV) that have both the right MHC receptor and the right peptide are lysed.

Together, the data demonstrate that CTL activity can be elicited by immunization with microparticles containing DNA that encodes a VSV peptide, and the lysis is MHC restricted and peptide specific. In other words, only the right peptide with the right MHC receptor is recognized by the T cell receptor of the CTL generated by immunization in accordance with the invention. This demonstrated that the microparticles serve the desired function.

Figure 6:
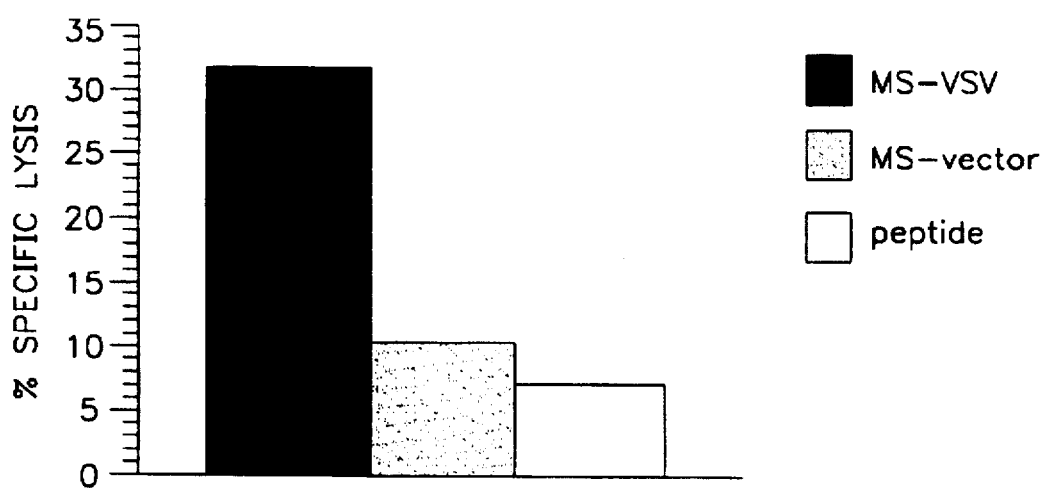

Next, the CTL response generated by immunizing mice subcutaneously with synthetic peptide (Group 8) was compared with the CTL response generated by immunizing mice intraperitoneally with microparticles containing DNA that encodes the VSV peptide (Groups 1 and 2). In FIG. 6 is shown the lysis obtained at a E:T ratio of 100:1 for CTL generated by immunizing the mice with either microparticles including DNA that encodes the VSV-N peptide (MS-VSV; Group 1), microparticles including control vector DNA that does not encode a VSV peptide (MS-vector; Group 2), or synthetic VSV-N peptide (peptide; Group 8). The targets were syngeneic (EL4) cells labelled with VSV peptide.

Mice immunized with the VSV-Npep DNA in microparticles (MS-VSV) generated a stronger CTL response (33% specific lysis) than mice immunized with control microparticles containing empty vector DNA (MS-vector) (10% specific lysis). Mice immunized with VSV-N peptide (peptide) generate a weaker CTL response than those immunized with microparticles containing VSV-Npep DNA (MS-VSV). Therefore, the microparticles served the desired function.

Figure 7:
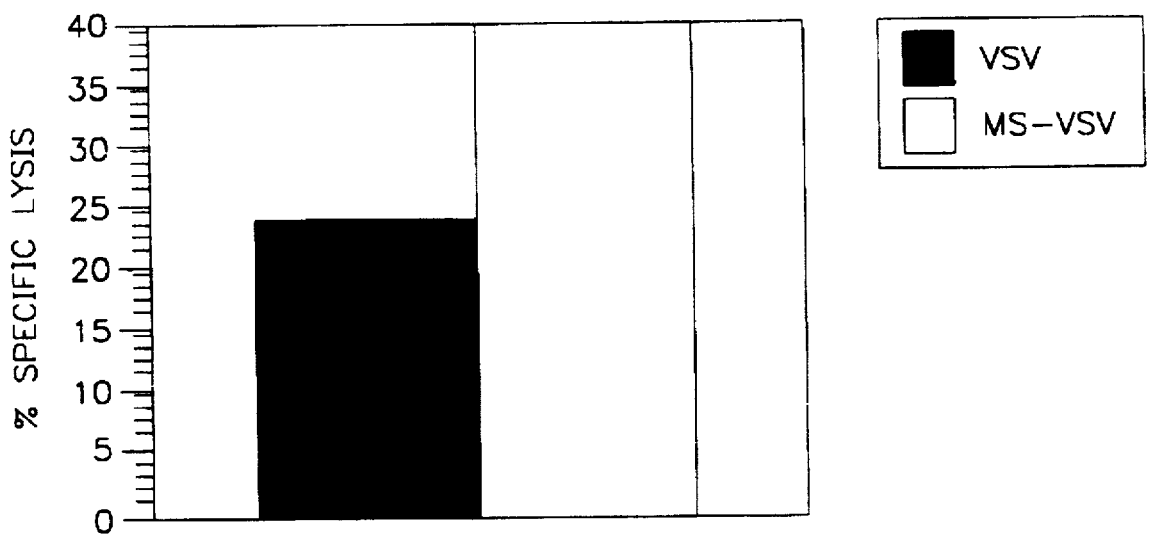

CTL responses in mice immunized intraperitoneally with VSV-Npep DNA contained in microparticles (MS-VSV) were compared with the CTL responses of mice immunized intramuscularly with "naked" VSV DNA (VSV). CTL responses in mice immunized with the microparticles containing DNA (MS-VSV; Group 1) were stronger than those in mice immunized with naked DNA (VSV; Group 5) at an E:T ratio of 3:1 (FIG. 7). The targets were syngeneic (EL4) cells labelled with VSV peptide. The mice which received naked DNA were immunized twice, while the mice immunized with microparticles were only given one treatment. The data in FIG. 7 therefore show that one injection of DNA in microparticles was more effective than two injections of a greater amount of naked DNA.

Figure 8:
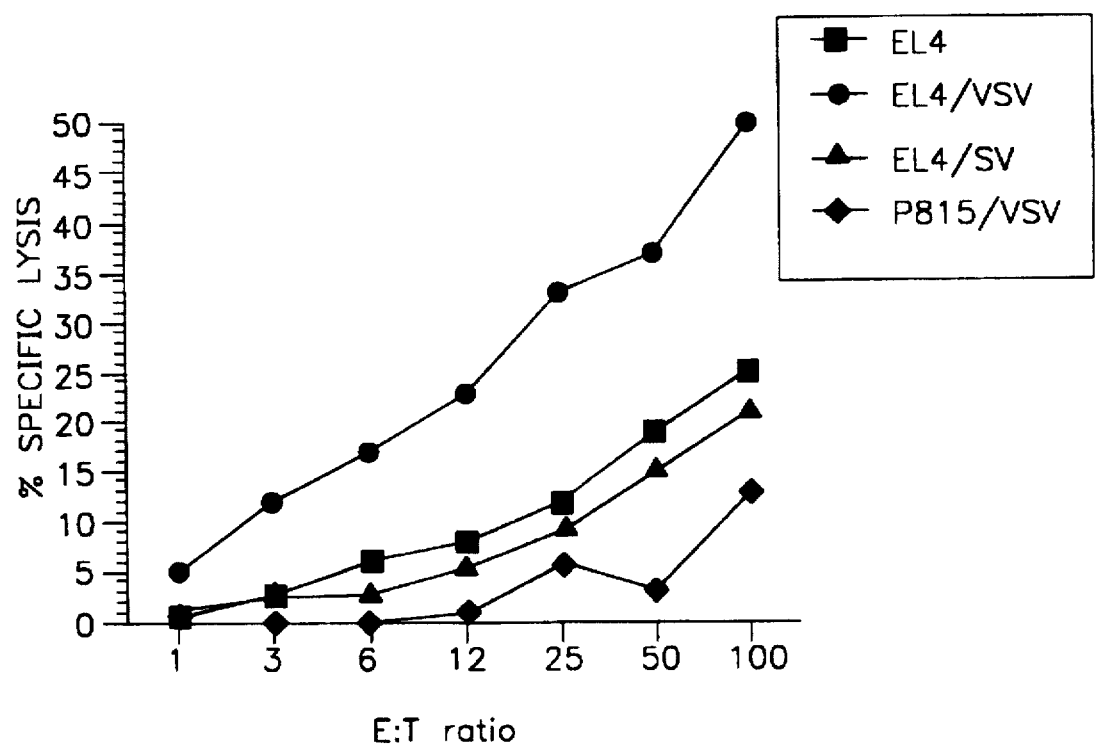

FIG. 8 shows the results of an experiment equivalent to that related in FIG. 5, with the exception that the injections were subcutaneous (Group 7 mice) instead of intraperitoneal. This experiment demonstrated that subcutaneous injections of microparticles containing VSV-Npep DNA are also effective for producing CTL responses.

Figure 9:
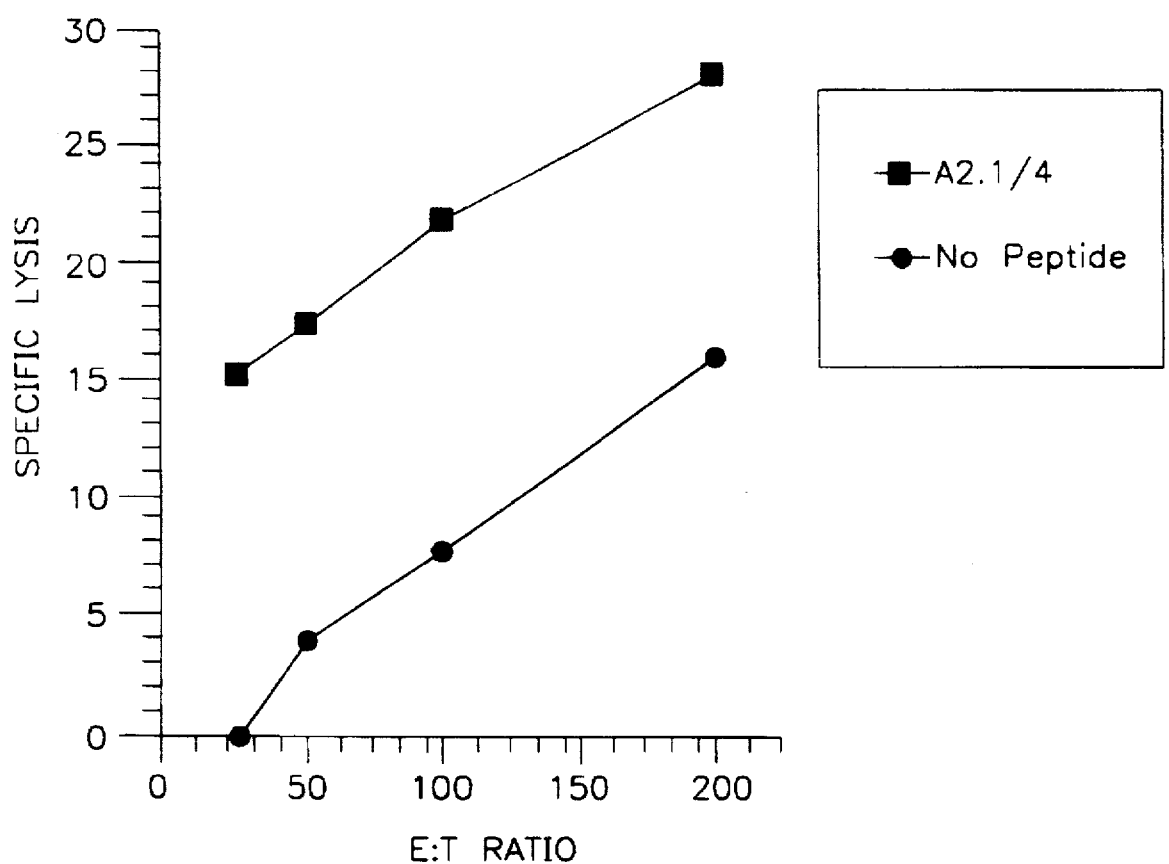

The experiment illustrated in FIG. 9 is also similar to that of FIG. 5, except that DNA encoding a different peptide was used in order to demonstrate that the results obtained were not unique to VSV-Npep DNA. HLA-A2 transgenic mice were immunized with microparticles containing DNA that encodes a peptide from human papillomavirus (HPV) E6 peptide. The HPV E6 peptide termed A2.1/4 binds to the human MHC receptor HLA-A2. The experiment assessed the ability of CTL effectors to lyse syngeneic targets (i.e., targets having the correct HLA receptor) that were either labeled with the correct HPV peptide (A2.1/4) or else unlabeled (no peptide). The E:T ratios are listed along the X-axis.

EXAMPLE 4
Treatment with Microparticles Containing DNA

According to the procedure of example 1, microparticles are prepared containing DNA encoding a peptide having an amino acid sequence about 50% identical to PLP residues 170–191 (SEQ ID NO: 2). A multiple sclerosis patient whose T cells secrete excess $T_H1$ cytokines (i.e., IL-2 and γ-IFN) in response to autoantigens is injected intravenously with 100 μl to 10 ml of the microparticles. Expression of the PLP-like peptide by APCs results in the switching of the cytokine profile of the T cells, such that they instead produce $T_H2$ cytokines (i.e., IL-4 and IL-10) in response to autoantigens.

EXAMPLE 5

Tolerizing with Microparticles Containing DNA

According to the procedure of example 1, microparticles are prepared containing DNA encoding a peptide having an amino acid sequence corresponding to MBP residues 33–52 (SEQ ID NO: 34). A mammal is injected subcutaneously with 50–500 μl of the microparticles. Expression of the MBP peptide by APCs results in the tolerization of T cells that recognize the autoantigen.

EXAMPLE 6

Implantation of Microparticles

A DNA molecule, including an expression control sequence operatively linked to a sequence encoding both a trafficking sequence and a peptide essentially identical to myelin basic protein (MBP) residues 80–102 (SEQ ID NO: 1), is associated with a polymer to form microparticles, according to the procedure of example 1. Particles smaller than 100 μm are removed. The polymeric constituent of the microparticle is poly-lactic-co-glycolic acid, where the ratio of lactic acid to glycolic acid is 65:35 by weight. The resulting microparticles are surgically implanted subcutaneously in a patient.

EXAMPLE 7

Preparation of Microparticles Containing Both DNA and Protein

Plasmid DNA is prepared by standard methods using MEGA-PREP™ Kit (Qiagen) according to the manufacturer's instructions. An endotoxin-free buffer kit (Qiagen) is used for all DNA manipulations. The DNA is resuspended in distilled, deionized, sterile water to give a final concentration of 3 μg/μl. Additionally, 0–40 mg of purified protein is added to about 1 ml of the DNA solution. A mass of gelatin, equal to about 20% of the mass of protein, is added.

Up to 400 mg of PLGA (i.e., at least ten times the mass of protein) is dissolved in about 7 ml methylene chloride. The DNA/protein solution is poured into the PLGA solution and homogenized or sonicated to form a first emulsion. The first emulsion is poured into about 50–100 ml of an aqueous solution of surfactant (e.g., 0.05% to 2% PVA by weight). The mixture is homogenized at about 3000–8000 RPM to form a second emulsion. The microparticles are then isolated according to the procedure of example 1.

EXAMPLE 8

Treatment with Microparticles Containing Both DNA and Protein

Microparticles including both an antigenic protein having the conformational determinants necessary for induction of B cell response against hepatitis B virus (HBV) and DNA encoding the CTL epitope for HBV, are prepared according to the procedure of example 6. A patient infected or at risk of infection with HBV is immunized with the microparticles.

Slow release of the protein from non-phagocytosed microparticles leads to B cell recognition of the conformational determinants and subsequent secretion of antibody. Slow release of the DNA or phagocytosis of other microparticles causes APCs (1) to express the DNA of interest, thereby generating a T cell response; and (2) to digest the protein released from the microparticles, thereby generating peptides which are subsequently presented by class I or II molecules. Presentation by class I molecules promotes CTL response; presentation by class II molecules promotes both antibody and T cell responses, since $T_H$ cells activated by the class II/peptide complexes secrete non-specific cytokines.

The results are elimination of HBV from the patient and continued prevention of production of virus within the patient's cells.

Other Embodiments

It is to be understood that while the invention has been described in conjunction with the detailed description thereof, that the foregoing description is intended to illustrate and not limit the scope of the appended claims. Other aspects, advantages, and modifications are within the scope of the following claims.

What is claimed is:

1. A preparation of microparticles, each of which comprises a polymeric matrix and nucleic acid, the polymeric matrix consisting essentially of one or more synthetic polymers having a solubility in water of less than about 1 mg/l, wherein
    at least 90% of the microparticles have a diameter less than about 100 microns, and
    the nucleic acid is an expression vector selected from the group consisting of RNA molecules, at least 50% of which are closed circles; and circular plasmid DNA molecules, at least 50% of which are supercoiled.

2. A microparticle less than about 20 microns in diameter, comprising:
    a polymeric matrix consisting essentially of one or more synthetic polymers having a solubility in water of less than about 1 mg/l; and
    nucleic acid molecules, at least 50% of which are supercoiled DNA.

3. The microparticle of claim 2, wherein the polymeric matrix is biodegradable.

4. The microparticle of claim 2, wherein the polymeric matrix consists essentially of one synthetic, biodegradable copolymer.

5. The microparticle of claim 4, wherein the copolymer is poly-lactic-co-glycolic acid (PLGA).

6. The microparticle of claim 2, wherein the microparticle has a diameter of less than about 11 microns.

7. The microparticle of claim 2, wherein the nucleic acid molecule comprises an expression control sequence operatively linked to a coding sequence.

8. A microparticle less than about 20 microns in diameter, comprising:
    a polymeric matrix; and
    a nucleic acid molecule comprising an expression control sequence operatively linked to a coding sequence encoding an expression product comprising a polypeptide at least 7 amino acids in length, said polypeptide having the sequence of (a) a fragment of a naturally-occurring mammalian protein or (b) a fragment of a naturally-occurring protein from an infectious agent which infects a mammal, wherein the expression product includes (i) part but not all of the naturally-occurring mammalian protein or (ii) part but not all of the naturally-occurring protein from an infectious agent.

9. The microparticle of claim 8, wherein the polyeptide is immunogenic.

10. The microparticle of claim 8, wherein the expression product (1) comprises an amino acid sequence of a naturally occurring peptide recognized by a T cell; (2) is recognized by the T cell; and (3) alters the cytokine profile of the T cell.

11. A method of administering nucleic acid to an animal, comprising providing the microparticle of claim 8; and introducing the microparticle into the animal.

12. A microparticle less than about 20 microns in diameter, comprising:

a polymeric matrix; and a nucleic acid molecule comprising an expression control sequence operatively linked to a coding sequence, wherein the coding sequence encodes a protein which, when expressed in a macrophage, downregulates an immune response in an animal.

13. A process for preparing microparticles, comprising:

(1) providing a first solution comprising a polymer dissolved in an organic solvent;

(2) providing a second solution comprising a nucleic acid dissolved or suspended in a polar or hydrophilic solvent;

(3) mixing the first and second solutions to form a first emulsion; and (4) mixing the first emulsion with a third solution comprising an organic compound, to form a second emulsion comprising microparticles of polymeric matrix and nucleic acid; wherein both mixing steps are carried out in a manner that minimizes shearing of the nucleic acid while producing microparticles having a number average smaller than 100 microns in diameter.

14. A method of administering nucleic acid to an animal, comprising providing the microparticle of claim 2; and introducing the microparticle into the animal.

15. A preparation of microparticles, each of which comprises:

a polymeric matrix;

a proteinaceous antigenic determinant; and

DNA which encodes an antigenic polypeptide.

16. The preparation of claim 15, wherein said antigenic determinant elicits an antibody response in a mammal.

17. The preparation of claim 15, wherein said antigenic polypeptide elicits a T cell response.

18. The preparation of claim 17, wherein said T cell response is a cytotoxic T cell (CTL) response.

19. The preparation of claim 15, wherein said DNA is plasmid DNA.

20. A method of administering nucleic acid to an animal, comprising providing the preparation of claim 15; and introducing the preparation into the animal.

21. A microparticle less than about 20 microns in diameter, comprising:

a polymeric matrix; and a nucleic acid molecule comprising an expression control sequence operatively linked to a coding sequence encoding an expression product comprising a trafficking sequence linked to a polypeptide, said polypeptide being at least 7 amino acids in length and having the sequence of (a) a fragment of a naturally-occurring mammalian protein or (b) a fragment of a naturally-occurring protein from an infectious agent which infects a mammal, wherein the expression product includes (i) part but not all of the naturally-occurring mammalian protein or (ii) part but not all of the naturally-occurring protein from an infectious agent.

22. The microparticle of claim 21, wherein the polypeptide is immunogenic.

23. The microparticle of claim 21, wherein the polypeptide (1) is recognized by a T cell; and (2) alters the cytokine profile of the T cell.

24. A microparticle less than about 20 microns in diameter, comprising:

a polymeric matrix; and a nucleic acid molecule comprising an expression control sequence operatively linked to a coding sequence encoding an expression product having a length and sequence which permit it to bind to an MHC class I or II molecule.

25. The microparticle of claim 24, wherein the expression product is immunogenic.

26. The microparticle of claim 24, wherein the expression product (1) is recognized by a T cell; and (2) alters the cytokine profile of the T cell.

27. A microparticle less than about 20 microns in diameter, comprising:

a polymeric matrix; and a nucleic acid molecule comprising an expression control sequence operatively linked to a coding sequence encoding an expression product consisting of a trafficking sequence linked to a peptide having a length and sequence which permit it to bind to an MHC class I or II molecule.

28. The microparticle of claim 27, wherein the peptide is immunogenic.

29. The microparticle of claim 27, wherein the peptide (1) is recognized by a T cell, and (2) alters the cytokine profile of the T cell.

30. A method of administering nucleic acid to an animal, comprising providing the microparticle of claim 21; and introducing the microparticle into the animal.

31. A method of administering nucleic acid to an animal, comprising providing the microparticle of claim 24; and introducing the microparticle into the animal.

32. A method of administering nucleic acid to an animal, comprising providing the microparticle of claim 27; and introducing the microparticle into the animal.

* * * * *

SEQUENCE LISTING ( 1 ) GENERAL INFORMATION:

( i i i ) NUMBER OF SEQUENCES: 107

( 2 ) INFORMATION FOR SEQ ID NO:1:

( i ) SEQUENCE CHARACTERISTICS:
( A ) LENGTH: 23 amino acids
( B ) TYPE: amino acid
( D ) TOPOLOGY: linear ( i i ) MOLECULE TYPE: peptide ( x i ) SEQUENCE DESCRIPTION: SEQ ID NO:1:

```
Gly Arg Thr Gln Asp Glu Asn Pro Val Val His Phe Phe Lys Asn Ile
1               5                   10                  15
```

```
Val Thr Pro Arg Thr Pro Pro
                20
```

( 2 ) INFORMATION FOR SEQ ID NO:2:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Ala Val Tyr Val Tyr Ile Tyr Phe Asn Thr Trp Thr Thr Cys Gln Phe
 1           5                   10                  15
Ile Ala Phe Pro Phe Lys
                20
```

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Phe Lys Met Arg Met Ala Thr Pro Leu Leu Met Gln Ala
 1           5                   10
```

( 2 ) INFORMATION FOR SEQ ID NO:4:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Thr Val Gly Leu Gln Leu Ile Gln Leu Ile Asn Val Asp Glu Val Asn
 1           5                   10                  15
Gln Ile Val Thr Thr Asn Val Arg Leu Lys Gln Gln Trp Val Asp Tyr
                20                  25                  30
Asn Leu Lys Trp
            35
```

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Gln Ile Val Thr Thr Asn Val Arg Leu Lys Gln Gln Trp Val Asp Tyr
 1           5                   10                  15
Asn Leu Lys Trp
            20
```

( 2 ) INFORMATION FOR SEQ ID NO:6:

( i ) SEQUENCE CHARACTERISTICS:
        ( A ) LENGTH: 7 amino acids (B) TYPE: amino acid
(D) TOPOLOGY: linear (ii) MOLECULE TYPE: peptide (xi) SEQUENCE DESCRIPTION: SEQ ID NO:6:

Gln Trp Val Asp Tyr Asn Leu
 1               5

(2) INFORMATION FOR SEQ ID NO:7:

(i) SEQUENCE CHARACTERISTICS:
    (A) LENGTH: 18 amino acids
    (B) TYPE: amino acid
    (D) TOPOLOGY: linear (ii) MOLECULE TYPE: peptide (xi) SEQUENCE DESCRIPTION: SEQ ID NO:7:

Gly Gly Val Lys Lys Ile His Ile Pro Ser Glu Lys Ile Trp Arg Pro
 1               5                   10                  15
Asp Leu (2) INFORMATION FOR SEQ ID NO:8:

(i) SEQUENCE CHARACTERISTICS:
    (A) LENGTH: 12 amino acids
    (B) TYPE: amino acid
    (D) TOPOLOGY: linear (ii) MOLECULE TYPE: peptide (xi) SEQUENCE DESCRIPTION: SEQ ID NO:8:

Ala Ile Val Lys Phe Thr Lys Val Leu Leu Gln Tyr
 1               5                   10

(2) INFORMATION FOR SEQ ID NO:9:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO:9:

Trp Thr Pro Pro Ala Ile Phe Lys Ser Tyr Cys Glu Ile Ile Val Thr
 1               5                   10                  15
His Phe Pro Phe
             20

(2) INFORMATION FOR SEQ ID NO:10:

(i) SEQUENCE CHARACTERISTICS:
    (A) LENGTH: 13 amino acids
    (B) TYPE: amino acid
    (D) TOPOLOGY: linear (ii) MOLECULE TYPE: peptide (xi) SEQUENCE DESCRIPTION: SEQ ID NO:10:

Met Lys Leu Gly Thr Trp Thr Tyr Asp Gly Ser Val Val
 1               5                   10

(2) INFORMATION FOR SEQ ID NO:11:

(i) SEQUENCE CHARACTERISTICS:
    (A) LENGTH: 13 amino acids (B) TYPE: amino acid
(D) TOPOLOGY: linear (ii) MOLECULE TYPE: peptide (xi) SEQUENCE DESCRIPTION: SEQ ID NO:11:

Met Lys Leu Gly Ile Trp Thr Tyr Asp Gly Ser Val Val
 1               5                   10

(2) INFORMATION FOR SEQ ID NO:12:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:12:

Trp Thr Tyr Asp Gly Ser Val Val Ala
 1               5

(2) INFORMATION FOR SEQ ID NO:13:

(i) SEQUENCE CHARACTERISTICS:
(A) LENGTH: 17 amino acids
(B) TYPE: amino acid
(D) TOPOLOGY: linear (ii) MOLECULE TYPE: peptide (xi) SEQUENCE DESCRIPTION: SEQ ID NO:13:

Ser Cys Cys Pro Asp Thr Pro Tyr Leu Asp Ile Thr Tyr His Phe Val
 1               5                   10                  15
Met (2) INFORMATION FOR SEQ ID NO:14:

(i) SEQUENCE CHARACTERISTICS:
(A) LENGTH: 18 amino acids
(B) TYPE: amino acid
(D) TOPOLOGY: linear (ii) MOLECULE TYPE: peptide (xi) SEQUENCE DESCRIPTION: SEQ ID NO:14:

Asp Thr Pro Tyr Leu Asp Ile Thr Tyr His Phe Val Met Gln Arg Leu
 1               5                   10                  15
Pro Leu (2) INFORMATION FOR SEQ ID NO:15:

(i) SEQUENCE CHARACTERISTICS:
(A) LENGTH: 21 amino acids
(B) TYPE: amino acid
(D) TOPOLOGY: linear (ii) MOLECULE TYPE: peptide (xi) SEQUENCE DESCRIPTION: SEQ ID NO:15:

Phe Ile Val Asn Val Ile Ile Pro Cys Leu Leu Phe Ser Phe Leu Thr
 1               5                   10                  15
Gly Leu Val Phe Tyr
             20

(2) INFORMATION FOR SEQ ID NO:16:

( i ) SEQUENCE CHARACTERISTICS:
   ( A ) LENGTH: 13 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:16:

Leu Leu Val Ile Val Glu Leu Ile Pro Ser Thr Ser Ser
1               5                   10

( 2 ) INFORMATION FOR SEQ ID NO:17:

( i ) SEQUENCE CHARACTERISTICS:
      ( A ) LENGTH: 19 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:17:

Ser Thr His Val Met Pro Asn Trp Val Arg Lys Val Phe Ile Asp Thr
1               5                   10                  15

Ile Pro Asn ( 2 ) INFORMATION FOR SEQ ID NO:18:

( i ) SEQUENCE CHARACTERISTICS:
      ( A ) LENGTH: 18 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:18:

Asn Trp Val Arg Lys Val Phe Ile Asp Thr Ile Pro Asn Ile Met Phe
1               5                   10                  15

Phe Ser ( 2 ) INFORMATION FOR SEQ ID NO:19:

( i ) SEQUENCE CHARACTERISTICS:
      ( A ) LENGTH: 18 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:19:

Ile Pro Asn Ile Met Phe Phe Ser Thr Met Lys Arg Pro Ser Arg Glu
1               5                   10                  15

Lys Gln ( 2 ) INFORMATION FOR SEQ ID NO:20:

( i ) SEQUENCE CHARACTERISTICS:
      ( A ) LENGTH: 16 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:20:

Ala Ala Ala Glu Trp Lys Tyr Val Ala Met Val Met Asp His Ile Leu
1               5                   10                  15

( 2 ) INFORMATION FOR SEQ ID NO:21:

(i) SEQUENCE CHARACTERISTICS:
  (A) LENGTH: 19 amino acids
  (B) TYPE: amino acid
  (D) TOPOLOGY: linear (ii) MOLECULE TYPE: peptide (xi) SEQUENCE DESCRIPTION: SEQ ID NO:21:

Ile Ile Gly Thr Leu Ala Val Phe Ala Gly Arg Leu Ile Glu Leu Asn
1               5                   10                  15
Gln Gln Gly (2) INFORMATION FOR SEQ ID NO:22:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO:22:

Gly Gln Thr Ile Glu Trp Ile Phe Ile Asp Pro Glu Ala Phe Thr Glu
1               5                   10                  15
Asn Gly Glu Trp
            20

(2) INFORMATION FOR SEQ ID NO:23:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO:23:

Met Ala His Tyr Asn Arg Val Pro Ala Leu Pro Phe Pro Gly Asp Pro
1               5                   10                  15
Arg Pro Tyr Leu
            20

(2) INFORMATION FOR SEQ ID NO:24:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (xi) SEQUENCE DESCRIPTION: SEQ ID NO:24:

Leu Asn Ser Lys Ile Ala Phe Lys Ile Val Ser Gln Glu Pro Ala
1               5                   10                  15

(2) INFORMATION FOR SEQ ID NO:25:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (xi) SEQUENCE DESCRIPTION: SEQ ID NO:25:

Thr Pro Met Phe Leu Leu Ser Arg Asn Thr Gly Glu Val Arg Thr
1               5                   10                  15

( 2 ) INFORMATION FOR SEQ ID NO:26:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

```
Pro Leu Gly Phe Phe Pro Asp His Gln Leu Asp Pro Ala Phe Gly Ala
  1               5                  10                  15
```

( 2 ) INFORMATION FOR SEQ ID NO:27:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

```
Leu Gly Phe Phe Pro Asp His Gln Leu Asp Pro Ala Phe Gly Ala Asn
  1               5                  10                  15
Ser
```

( 2 ) INFORMATION FOR SEQ ID NO:28:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

```
Phe Phe Leu Leu Thr Arg Ile Leu Thr Ile
  1               5                  10
```

( 2 ) INFORMATION FOR SEQ ID NO:29:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:29:

```
Arg Ile Leu Thr Ile Pro Gln Ser Leu Asp
  1               5                  10
```

( 2 ) INFORMATION FOR SEQ ID NO:30:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:30:

```
Thr Pro Thr Leu Val Glu Val Ser Arg Asn Leu Gly Lys
  1               5                  10
```

( 2 ) INFORMATION FOR SEQ ID NO:31:

( i ) SEQUENCE CHARACTERISTICS:
   ( A ) LENGTH: 12 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:31:

Ala Lys Thr Ile Ala Tyr Asp Glu Glu Ala Arg Arg
 1               5                  10

( 2 ) INFORMATION FOR SEQ ID NO:32:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:32:

Val Val Thr Val Arg Ala Glu Arg Pro Gly
 1               5                  10

( 2 ) INFORMATION FOR SEQ ID NO:33:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:33:

Ser Gln Arg His Gly Ser Lys Tyr Leu Ala Thr Ala Ser Thr Met Asp
 1               5                  10                  15

His Ala Arg His Gly
            20

( 2 ) INFORMATION FOR SEQ ID NO:34:

( i ) SEQUENCE CHARACTERISTICS:
      ( A ) LENGTH: 20 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:34:

Arg Asp Thr Gly Ile Leu Asp Ser Ile Gly Arg Phe Phe Gly Gly Asp
 1               5                  10                  15

Arg Gly Ala Pro
            20

( 2 ) INFORMATION FOR SEQ ID NO:35:

( i ) SEQUENCE CHARACTERISTICS:
      ( A ) LENGTH: 20 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:35:

Gln Lys Ser His Gly Arg Thr Gln Asp Glu Asn Pro Val Val His Phe
 1               5                  10                  15

Phe Lys Asn Ile

20

( 2 ) INFORMATION FOR SEQ ID NO:36:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:36:

```
Asp Glu Asn Pro Val Val His Phe Phe Lys Asn Ile Val Thr
 1               5                  10
```

( 2 ) INFORMATION FOR SEQ ID NO:37:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:37:

```
Glu Asn Pro Val Val His Phe Phe Lys Asn Ile Val Thr Pro Arg
 1               5                  10                  15
```

( 2 ) INFORMATION FOR SEQ ID NO:38:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:38:

```
His Phe Phe Lys Asn Ile Val Thr Pro Arg Thr Pro Pro
 1               5                  10
```

( 2 ) INFORMATION FOR SEQ ID NO:39:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:39:

```
Lys Gly Phe Lys Gly Val Asp Ala Gln Gly Thr Leu Ser Lys
 1               5                  10
```

( 2 ) INFORMATION FOR SEQ ID NO:40:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:40:

```
Val Asp Ala Gln Gly Thr Leu Ser Lys Ile Phe Lys Leu Gly Gly Arg
 1               5                  10                  15
Asp Ser Arg Ser
                20
```

( 2 ) INFORMATION FOR SEQ ID NO:41:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:41:

Leu Met Gln Tyr Ile Asp Ala Asn Ser Lys Phe Ile Gly Ile Thr Glu
1               5                   10                  15
Leu Lys Lys ( 2 ) INFORMATION FOR SEQ ID NO:42:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:

Gln Tyr Ile Lys Ala Asn Ser Lys Phe Ile Gly Ile Thr
1               5                   10

( 2 ) INFORMATION FOR SEQ ID NO:43:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:43:

Phe Asn Asn Phe Thr Val Ser Phe Trp Leu Arg Val Pro Lys
1               5                   10

( 2 ) INFORMATION FOR SEQ ID NO:44:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:44:

Ser Phe Trp Leu Arg Val Pro Lys Val Ser Ala Ser His Leu Glu
1               5                   10                  15

( 2 ) INFORMATION FOR SEQ ID NO:45:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:45:

Lys Phe Ile Ile Lys Arg Tyr Thr Pro Asn Asn Glu Ile Asp Ser Phe
1               5                   10                  15

( 2 ) INFORMATION FOR SEQ ID NO:46:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:46:

Gly Gln Ile Gly Asn Asp Pro Asn Arg Asp Ile Leu
1               5                   10

( 2 ) INFORMATION FOR SEQ ID NO:47:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:47:

Ala Ala Arg Ala Val Phe Leu Ala Leu
1               5

( 2 ) INFORMATION FOR SEQ ID NO:48:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:48:

Tyr Arg Pro Arg Pro Arg Arg Tyr
1               5

( 2 ) INFORMATION FOR SEQ ID NO:49:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:49:

Glu Ala Asp Pro Thr Gly His Ser Tyr
1               5

( 2 ) INFORMATION FOR SEQ ID NO:50:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:50:

Ser Ala Tyr Gly Glu Pro Arg Lys Leu
1               5

( 2 ) INFORMATION FOR SEQ ID NO:51:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:51:

Glu Val Asp Pro Ile Gly His Leu Tyr
1               5

( 2 ) INFORMATION FOR SEQ ID NO:52:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:52:

Phe Leu Trp Gly Pro Arg Ala Leu Val
1               5

( 2 ) INFORMATION FOR SEQ ID NO:53:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:53:

Gly Ile Gly Ile Leu Thr Val
1               5

( 2 ) INFORMATION FOR SEQ ID NO:54:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:54:

Ile Leu Thr Val Ile Leu Gly Val
1               5

( 2 ) INFORMATION FOR SEQ ID NO:55:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:55:

Ser Thr Ala Pro Pro Ala His Gly Val
1               5

( 2 ) INFORMATION FOR SEQ ID NO:56:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:56:

Glu Glu Lys Leu Ile Val Val Leu Phe (2) INFORMATION FOR SEQ ID NO:57:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:57:

Met Leu Leu Ala Val Leu Tyr Cys Leu
1                      5

(2) INFORMATION FOR SEQ ID NO:58:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:58:

Ser Glu Ile Trp Arg Asp Ile Asp Phe
1                      5

(2) INFORMATION FOR SEQ ID NO:59:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:59:

Ala Phe Leu Pro Trp His Arg Leu Phe
1                      5

(2) INFORMATION FOR SEQ ID NO:60:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:60:

Tyr Met Asn Gly Thr Met Ser Gln Val
1                      5

(2) INFORMATION FOR SEQ ID NO:61:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:61:

Lys Thr Trp Gly Gln Tyr Trp Gln Val
1                      5

(2) INFORMATION FOR SEQ ID NO:62:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:62:

Ile Thr Asp Gln Val Pro Phe Ser Val
1               5

( 2 ) INFORMATION FOR SEQ ID NO:63:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:63:

Tyr Leu Glu Pro Gly Pro Thr Val Ala
1               5

( 2 ) INFORMATION FOR SEQ ID NO:64:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:64:

Leu Leu Asp Gly Thr Ala Thr Leu Arg Leu
1               5                   10

( 2 ) INFORMATION FOR SEQ ID NO:65:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:65:

Glu Leu Asn Glu Ala Leu Glu Leu Glu Lys
1               5                   10

( 2 ) INFORMATION FOR SEQ ID NO:66:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:66:

Ser Thr Pro Pro Pro Gly Thr Arg Val
1               5

( 2 ) INFORMATION FOR SEQ ID NO:67:

( i ) SEQUENCE CHARACTERISTICS:
    ( A ) LENGTH: 11 amino acids
    ( B ) TYPE: amino acid
    ( D ) TOPOLOGY: linear (i i) MOLECULE TYPE: peptide (x i) SEQUENCE DESCRIPTION: SEQ ID NO:67:

```
Leu Leu Pro Glu Asn Asn Val Leu Ser Pro Leu
 1               5                    10
```

(2) INFORMATION FOR SEQ ID NO:68:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (x i) SEQUENCE DESCRIPTION: SEQ ID NO:68:

```
Leu Leu Gly Arg Asn Ser Phe Glu Val
 1               5
```

(2) INFORMATION FOR SEQ ID NO:69:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (x i) SEQUENCE DESCRIPTION: SEQ ID NO:69:

```
Arg Met Pro Glu Ala Ala Pro Pro Val
 1               5
```

(2) INFORMATION FOR SEQ ID NO:70:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (x i) SEQUENCE DESCRIPTION: SEQ ID NO:70:

```
Lys Ile Phe Gly Ser Leu Ala Phe Leu
 1               5
```

(2) INFORMATION FOR SEQ ID NO:71:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (x i) SEQUENCE DESCRIPTION: SEQ ID NO:71:

```
Ile Ile Ser Ala Val Val Gly Ile Leu
 1               5
```

(2) INFORMATION FOR SEQ ID NO:72:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (x i) SEQUENCE DESCRIPTION: SEQ ID NO:72:

```
Cys Leu Thr Ser Thr Val Gln Leu Val
```

1          5

(2) INFORMATION FOR SEQ ID NO:73:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:73:

Tyr  Leu  Glu  Asp  Val  Arg  Leu  Val
1                    5

(2) INFORMATION FOR SEQ ID NO:74:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:74:

Val  Leu  Val  Lys  Ser  Pro  Asn  His  Val
1                    5

(2) INFORMATION FOR SEQ ID NO:75:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:75:

Arg  Phe  Arg  Glu  Leu  Val  Ser  Glu  Phe  Ser  Arg  Met
1                    5                         10

(2) INFORMATION FOR SEQ ID NO:76:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:76:

Leu  Leu  Arg  Leu  Ser  Glu  Pro  Ala  Glu  Leu
1                    5                         10

(2) INFORMATION FOR SEQ ID NO:77:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:77:

Asp  Leu  Pro  Thr  Gln  Glu  Pro  Ala  Leu
1                    5

(2) INFORMATION FOR SEQ ID NO:78:

(i) SEQUENCE CHARACTERISTICS:
  (A) LENGTH: 9 amino acids
  (B) TYPE: amino acid
  (D) TOPOLOGY: linear (ii) MOLECULE TYPE: peptide (xi) SEQUENCE DESCRIPTION: SEQ ID NO:78:

Lys Leu Gln Cys Val Asp Leu His Val
 1               5

(2) INFORMATION FOR SEQ ID NO:79:

(i) SEQUENCE CHARACTERISTICS:
  (A) LENGTH: 10 amino acids
  (B) TYPE: amino acid
  (D) TOPOLOGY: linear (ii) MOLECULE TYPE: peptide (xi) SEQUENCE DESCRIPTION: SEQ ID NO:79:

Val Leu Val Ala Ser Arg Gly Arg Ala Val
 1               5                    10

(2) INFORMATION FOR SEQ ID NO:80:

(i) SEQUENCE CHARACTERISTICS:
  (A) LENGTH: 9 amino acids
  (B) TYPE: amino acid
  (D) TOPOLOGY: linear (ii) MOLECULE TYPE: peptide (xi) SEQUENCE DESCRIPTION: SEQ ID NO:80:

Val Leu Val His Pro Gln Trp Val Leu
 1               5

(2) INFORMATION FOR SEQ ID NO:81:

(i) SEQUENCE CHARACTERISTICS:
  (A) LENGTH: 10 amino acids
  (B) TYPE: amino acid
  (D) TOPOLOGY: linear (ii) MOLECULE TYPE: peptide (xi) SEQUENCE DESCRIPTION: SEQ ID NO:81:

Asp Met Ser Leu Leu Lys Asn Arg Phe Leu
 1               5                    10

(2) INFORMATION FOR SEQ ID NO:82:

(i) SEQUENCE CHARACTERISTICS:
  (A) LENGTH: 9 amino acids
  (B) TYPE: amino acid
  (D) TOPOLOGY: linear (ii) MOLECULE TYPE: peptide (xi) SEQUENCE DESCRIPTION: SEQ ID NO:82:

Gln Trp Asn Ser Thr Ala Phe His Gln
 1               5

(2) INFORMATION FOR SEQ ID NO:83:

(i) SEQUENCE CHARACTERISTICS:
  (A) LENGTH: 7 amino acids
  (B) TYPE: amino acid
  (D) TOPOLOGY: linear (i i) MOLECULE TYPE: peptide (x i) SEQUENCE DESCRIPTION: SEQ ID NO:83:

Val Leu Gln Ala Gly Phe Phe
1               5

(2) INFORMATION FOR SEQ ID NO:84:

(i) SEQUENCE CHARACTERISTICS:
        (A) LENGTH: 8 amino acids
        (B) TYPE: amino acid
        (D) TOPOLOGY: linear (i i) MOLECULE TYPE: peptide (x i) SEQUENCE DESCRIPTION: SEQ ID NO:84:

Leu Leu Leu Cys Leu Ile Phe Leu
1               5

(2) INFORMATION FOR SEQ ID NO:85:

(i) SEQUENCE CHARACTERISTICS:
        (A) LENGTH: 8 amino acids
        (B) TYPE: amino acid
        (D) TOPOLOGY: linear (i i) MOLECULE TYPE: peptide (x i) SEQUENCE DESCRIPTION: SEQ ID NO:85:

Leu Leu Asp Tyr Gln Gly Met Leu
1               5

(2) INFORMATION FOR SEQ ID NO:86:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (x i) SEQUENCE DESCRIPTION: SEQ ID NO:86:

Leu Leu Val Pro Phe Val
1               5

(2) INFORMATION FOR SEQ ID NO:87:

(i) SEQUENCE CHARACTERISTICS:
        (A) LENGTH: 10 amino acids
        (B) TYPE: amino acid
        (D) TOPOLOGY: linear (i i) MOLECULE TYPE: peptide (x i) SEQUENCE DESCRIPTION: SEQ ID NO:87:

Ser Ile Leu Ser Pro Phe Met Pro Leu Leu
1               5                   10

(2) INFORMATION FOR SEQ ID NO:88:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (x i) SEQUENCE DESCRIPTION: SEQ ID NO:88:

Pro Leu Leu Pro Ile Phe Phe Cys Leu ( 2 ) INFORMATION FOR SEQ ID NO:89:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:89:

```
Ile Leu Ser Thr Leu Pro Glu Thr Thr Val
 1               5                   10
```

( 2 ) INFORMATION FOR SEQ ID NO:90:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:90:

```
Phe Leu Pro Ser Asp Phe Phe Pro Ser Val
 1               5                   10
```

( 2 ) INFORMATION FOR SEQ ID NO:91:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:91:

```
Lys Leu His Leu Tyr Ser His Pro Ile
 1               5
```

( 2 ) INFORMATION FOR SEQ ID NO:92:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:92:

```
Ala Leu Met Pro Leu Tyr Ala Cys Ile
 1               5
```

( 2 ) INFORMATION FOR SEQ ID NO:93:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:93:

```
His Leu Tyr Ser His Pro Ile Ile Leu
 1               5
```

( 2 ) INFORMATION FOR SEQ ID NO:94:

( i ) SEQUENCE CHARACTERISTICS:
   ( A ) LENGTH: 9 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:94:

Phe Leu Leu Ser Leu Gly Ile His Leu
 1               5

( 2 ) INFORMATION FOR SEQ ID NO:95:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:95:

His Leu Leu Val Gly Ser Ser Gly Leu
 1               5

( 2 ) INFORMATION FOR SEQ ID NO:96:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:96:

Gly Leu Ser Arg Tyr Val Ala Arg Leu
 1               5

( 2 ) INFORMATION FOR SEQ ID NO:97:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:97:

Leu Leu Ala Gln Phe Thr Ser Ala Ile
 1               5

( 2 ) INFORMATION FOR SEQ ID NO:98:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:98:

Tyr Met Asp Asp Val Val Leu Gly Ala
 1               5

( 2 ) INFORMATION FOR SEQ ID NO:99:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:99:

Gly Leu Tyr Ser Ser Thr Val Pro Val
 1               5

( 2 ) INFORMATION FOR SEQ ID NO:100:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:100:

Asn Leu Ser Trp Leu Ser Leu Asp Val
 1               5

( 2 ) INFORMATION FOR SEQ ID NO:101:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:101:

Lys Leu Pro Gln Leu Cys Thr Glu Leu
 1               5

( 2 ) INFORMATION FOR SEQ ID NO:102:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:102:

Leu Gln Thr Thr Ile His Asp Ile Ile
 1               5

( 2 ) INFORMATION FOR SEQ ID NO:103:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:103:

Phe Ala Phe Arg Asp Leu Cys Ile Val
 1               5

( 2 ) INFORMATION FOR SEQ ID NO:104:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:104:

Tyr Met Leu Asp Leu Gln Pro Glu Thr

-continued (2) INFORMATION FOR SEQ ID NO:105:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:105:

Thr Leu His Glu Tyr Met Leu Asp Leu
1               5

(2) INFORMATION FOR SEQ ID NO:106:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:106:

Leu Leu Met Gly Thr Leu Gly Ile Val
1               5

(2) INFORMATION FOR SEQ ID NO:107:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:107:

Thr Leu Gly Ile Val Cys Pro Ile
1               5